United States Patent [19]
Kraus et al.

[11] Patent Number: 5,786,198
[45] Date of Patent: Jul. 28, 1998

[54] PHOTOACTIVATED ANTIVIRAL AND ANTITUMOR COMPOSITIONS

[75] Inventors: George A. Kraus; Susan L. Carpenter; Jacob W. Petrich, all of Story, Iowa

[73] Assignee: Iowa State University Research Foundation

[21] Appl. No.: 474,011

[22] Filed: Jun. 7, 1995

Related U.S. Application Data

[63] Continuation-in-part of Ser. No. 995,877, Dec. 23, 1992, abandoned.
[51] Int. Cl.$^6$ .............................. C12N 7/04; C12N 7/06; C07H 21/04
[52] U.S. Cl. ........................................ 435/236; 536/23.1
[58] Field of Search ............................ 435/236; 514/732, 514/738; 536/23.1

[56] References Cited

PUBLICATIONS

Lenard, et al., "Photodynamic inactivation of infectivity of human immunodeficiency virus and other enveloped viruses using hypericin and rose bengal: Inhibition of fusion and syncytia formation" *Proc. Natl. Acad. Sci. USA*, 90:158–162 (Jan. 1993)).

Van Steveninck et al., "Photodynamic Effects Induced by the Luciferin/Luciferase System," *Photochemistry and Photobiology*, 43:2, 213–216 (1986).

Carpenter et al., "Identification of a Hypervariable Region in the Long Terminal Repeat of Equine Infectious Anemia Virus," *Journal of Virology*, 65:3, 1605–1610 (Mar. 1991).

Kraus et al., "Antiretroviral Activity of Synthetic Hypericin and Related Analogs," *Biochemical and Biophysical Research Communications*, 172:149, 153 (Oct. 15, 1990).

Carpenter et al., "Photosensitization is Required for Inactivation of Equine Infectious Anemia Virus by Hypericin," *Photochemistry and Photobiology*, 53:2, 169–174 (1991).

John S. James, "Hypericin Update," *AIDS Treatment News*, 125:4–6 (Apr. 19, 1991).

John S. James, Hypericin, Feb. 1992, AIDS Treatment News 146:1–4 (Mar. 6, 1992).

Meruelo et al., "Therapeutic agents with dramatic antiretroviral activity and little toxicity at effective doses: Aromatic polycyclic diones hypericin and pseudohypericin," *Proc. Natl. Sci. USA*, 85:5230–5234 (Jul. 1988).

Matthews et al., "Photodynamic therapy of viral contaminants with potential for blood banking applications," *Transfusion*, 28:1, 81–83 (1988).

Lavie et al., "Studies of the mechanisms of action of the antiretroviral agents hypericin and pseudohypericin," *Proc. Natl. Acad. Sci USA*, 86:5963–5967 (Aug. 1989).

Chanh et al., "Photodydnamic liactivation of simian liunodeficiency virus," *Journal of Virological Methods*, 26:125–132 (1989).

Moan, J., "Yearly Review: Porphyrin Photosensitization and Phototherapy", *Photochemistry and Photobiology*, 43:6, 681–690 (1986).

"Luciferase Assay System," *Promega Technical Bulletin*, 101:12/.90.

"GeneLight™ Plasmids Technical Manual," *Promega*, #TM003, Oct. 1991.

Hudson et al., "Antiviral activities of hypericin," *Antiviral Research*, vol. 15, pp. 101–112 (1991).

Thomas et al., "Oxygen Dependence of Hypericin–Induced Phototoxicity to EMT6 Mouse Mammary Carcinoma Cells", *Photochemistry and Photobiology*, vol. 55, No. 6, pp. 831–837, 1992.

Culver et al., Lymphocytes as cellular vehicles for gene therapy in mouse and man, *Proc. Natl. Acad. Sci. USA*, vol. 88, pp. 3155–3159, Apr. 1991.

Cornetta et al., Protamine sulfate as an effective alternative to polybrene in retroviral–mediated gene–transfer: implications for human gene therapy, *Journal of Virological Methods*, 23 (1989) 187–194.

Kantoff et al., Expression of Human Adenosine Deaminase in Nonhuman Primates After Retrovirus–Mediated Gene Transfer, *The Rockefeller University Press*, vol. 166, pp. 219–234, Jul. 1987.

Kasid et al., Human gene transfer: Characterization of human tumor–infiltrating lymphocytes as vehicles for retroviral–mediated gene transfer in man, *Proc. Natl. Acad. Sci. USA*, vol. 87, pp. 473–477, Jan. 1990.

Kantoff et al., Correction of adenosine deaminase deficiency in cultured human T and B cells by retrovirus–mediated gene transfer, *Proc. Natl. Acad. Sci. USA*, vol. 83, pp. 6563–6567, Sep. 1986.

(List continued on next page.)

*Primary Examiner*—Nancy Degen
*Attorney, Agent, or Firm*—Dickstein Shapiro Morin & Oshinsky LLP

[57] ABSTRACT

Disclosed herein are compounds, compositions, and methods to inactivate a virus and destroy tumor cells. The methods involve the addition into the cell of a compound containing a photosensitizing chemical and an energy donating chemical, optionally linked by a chemical tether. Also introduced into the cell are means to chemically activate the energy donating chemical which photoactivates the photosensitizing chemical which then destroys the tumor or virus. The photosensitizing chemical is preferably hypericin, porphyrin, or an analog and the energy donating chemical is preferably luciferin or an analog. Methods for synthesizing the chemicals are also disclosed. Further, the energy donating chemical is activated by an activating chemical. The expression of the activating chemical is regulated so as to target the virus-infected or tumor cells. Regulating the activating chemical is accomplished by a number of methods including construction of an expression plasmid containing a gene encoding the activating chemical under control of a promoter which is transactivated by replication of the virus or transactivated by elevated levels of proteins expressed in tumor cells.

18 Claims, 6 Drawing Sheets

PUBLICATIONS

Lim et al., Retrovirus–Mediated Gene Transfer of Human Adenosine Deaminase: Expression of Functional Enzyme in Murine Hematopoietic Stem Cells in Vivo. *Molecular and Cellular Biology*, Oct. 1987, pp. 3459–3465 (1987).

Introduction of Recombinant Vectors into Mammalian Cells, *Expression of Cloned Genes in Cultured Mammalian Cells.*

Eli Gilboa, Retroviral Gene Transfer: Application to Human Therapy, *Retroviruses and Disease*, 1989.

Campbell, Ak et al. 1985. in Methods of Biochemical Analysis, David Glizk, ed. John Wiley & Sons. vol. 31 esp. pp. 317–345.

Schwartz, O., et al 1990. Gene vol. 80 pp. 197–205.

Liebes, L., et al. 1991. Analytical Biochemistry. vol. 195 pp. 77–85.

Shimomura, O., et al. 1978. Biochemistry vol. 17, No. 6, pp. 994–998.

Kraus, G.A., et al. 1990. Biochemical and Biophysical Research Communications, vol. 172, No. 1, pp. 149–153.

White, E.H., et al. 1975, J. of the American Chemical Society, vol. 97, No. 5, pp. 1243–1245.

PHOTOACTIVATED ANTIVIRAL AND ANTITUMOR COMPOSITIONS

The following is a continuation-in-part of U.S. patent application Ser. No. 07/995,877 filed Dec. 23, 1992, now abandoned.

FIELD OF THE INVENTION

This invention relates to compositions containing photodynamic molecules and means for activating the antiviral and antitumor properties of such molecules within viral-infected and tumor cells without an external light source.

BACKGROUND OF THE INVENTION

In recent years, photodynamic therapy (PDT) has emerged as a promising tool in both antiviral and cancer chemotherapy. In the presence of light of the appropriate wavelengths, the photoactive molecule absorbs the light and inactivates the virus or destroys the tumor cell. Photoactive molecules which are currently employed include a mixture of compounds called hematoporphyrin derivatives (HpD), the purpurins and the phthalocyanines. A major drawback is that PDT cannot be extended to treatment in regions of the body where light does not penetrate.

Moan et al., "Yearly Review: Porphyrin Photosensitization and Phototherapy," *Photochemistry and Photobiology:* Vol. 43, No. 6, pp. 681–690 (1986), which is incorporated herein in its entirety by reference, discloses the tumor localizing property of porphyrins and their use in PDT. The method of treatment involves direct injection of the photosensitizer. The photosensitizer molecules are affected by a light source located outside the body. Moan et al. specifically mention that because penetration of light is limited, PDT can never be used to eliminate large tumors.

Meruelo et al., "Therapeutic Agents With Dramatic Antiretroviral Activity and Little Toxicity at Effective Doses: Aromatic Polycyclic Diones Hypericin and Pseudohypericin," *Proc. Natl. Acad. Sci.*, Vol. 85, pp. 5230–5234 (1988), which is incorporated herein in its entirety by reference, have demonstrated that hypericin inhibits the replication of Friend leukemia virus and radiation leukemia virus, both in vitro and in vivo. Meruelo et al. stated that when hypericin was administered to mice at doses sufficient to prevent retroviral-induced disease, the mice appeared to be devoid of undesirable side effects. Meruelo et al. have also reported that hypericin can reduce the spread of HIV. Meruelo et al. speculate that hypericin may act by direct inactivation of the virions.

Chanh et al., "Photodynamic Inactivation of Simian Immunodeficiency Virus," *J. of Virological Methods*, Vol. 26, pp. 125–132 (1989), which is incorporated herein in its entirety by reference, disclose photodynamic inactivation of simian immunodeficiency virus (SIV). A dihematoporphyrin ether (DHE) was used to inactivate, in vitro, the infectivity of SIV. DHE was activated through the use of a laser beam. The experiment was conducted by incubating SIV suspended in a culture medium with DHE in the dark, followed by irradiation. The authors postulated that this treatment will reduce the risk of infection by enveloped viruses during transfusions.

Lavie et al., "Studies of Mechanisms of Action of the Antiretroviral Agents Hypericin and Pseudohypericin," *Proc. Natl. Acad. Sci.*, Vol. 86, pp. 5963–5967 (1989), which is incorporated herein in its entirety by reference, disclose that hypericin and pseudohypericin possess anti-retroviral activity. Specifically, the hypericin and pseudohypericin suppress the spread of murine retrovirus in vitro and in vivo. Treatment by hypericin and pseudohypericin resulted in complete inactivation of reverse transcriptase of both murine and human viruses when the compounds were administered by injection.

Hudson et al., "Antiviral Activities of Hypericin," *Antiviral Research*, Vol. 15, pp. 101–112 (1991), which is incorporated herein in its entirety by reference, disclose that hypericin inactivates murine cytomegalovirus (MCMV) Sindbis Virus, and HIV-1.

U.S. Pat. Nos. 4,898,891, 5,049,589 and 5,047,435 to Lavie et al., all of which are incorporated herein by reference, disclose the antiviral effects of hypericin and pseudohypericin and antiviral pharmaceutical composition containing hypericin as an active ingredient.

Finally, Matthews et al., "Photodynamic Therapy of Viral Contaminants with Potential for Blood Banking Applications," *Transfusion*, Vol. 28, No. 1, pp. 81–83 (1988), which is incorporated herein in its entirety by reference, disclose PDT for eradicating viral contaminants. The method employs a hematoporphyrin derivative used as the photosensitizer to inactivate an enveloped virus. The method involves extracorporeal plasmaphoresis, i.e., the blood is taken out of the body prior to being treated with hematoporphyrin and light. The method uses visible light.

There is a need to connect an energy source to photoactive molecules so that PDT can be expanded to all regions of the body. There is also a need to provide a method for targeting PDT to viral infected cells or to tumor cells.

Thus, activation of the energy source must be regulated such that activation preferentially occurs in the virus-infected cells or tumor cells. The present invention overcomes the problems in the prior art by employing an energy source which (1) emits energy in a broad band of wavelengths in the range in which the photoactive molecule absorbs and (2) is chemically activated by another chemical, which is regulated to express in the virus-infected or tumor cell. Thus, photoactivation of the photosensitizer is targeted to the virus-infected or tumor cells. The inventors have also developed chemical tethers to connect the energy source and the photoactive molecule. The use of such a tethered compound allows for the in vivo introduction of an internal chemically-activated light source having broad applications in antiviral and tumor therapy.

SUMMARY OF THE INVENTION

It is an object of the present invention to provide antiviral compositions.

It is a further object of the invention to provide tethered compounds for use in the antiviral compositions.

Another object of the invention is to provide antitumor compositions.

Another object of the invention is to provide tethered compounds for use in the antitumor compositions.

Another object of the invention is to provide hypericin analogs for use as intermediates in the preparation of the tethered compounds.

Another object of the invention is to provide luciferin and its analogs for use as intermediates in the preparation of the tethered compounds.

Yet another object of the invention is to provide methods for synthesizing precursors of the luciferin analogs.

Yet another object of the invention is to provide methods for synthesizing the tethered compounds.

A still further object of the invention is to provide means for activating the tethered compounds.

A still further object of the invention is to provide expression plasmids for activating the tethered compounds.

A still further object of the invention is to provide a liposome containing an expression plasmid.

A still further object of the invention is to provide a transfected cell containing an expression plasmid.

A still further object of the invention is to provide an eukaryotic cell containing a stably integrated copy of an expression plasmid.

A still further object of the invention is to provide a viral vector produced from the eukaryotic cell.

Additional objects and advantages of the invention will be set forth in part in the description which follows, and in part will be obvious from the description, or may be learned by the practice of the invention. The objects and advantages of the invention will be attained by means of the instrumentalities and combinations particularly pointed out in the appended claims.

To achieve the objects in accordance with the purpose of the invention as embodied and broadly described herein, the present invention provides a composition for inactivating a virus or destroying a tumor cell. The composition preferably contains three components. The first component is a chemical capable of photosensitization, hereinafter termed "a photosensitizing chemical." The second component is an energy donating chemical. The third component contains means for activating the transfer of energy or the emission of light from the energy donating chemical. The present invention preferably employs luciferin, a natural light source, or its analogs as the energy donating chemical. The photosensitizing chemical is preferably hypericin, a porphyrin, or one of their analogs.

In a preferred antiviral composition, as well as in a preferred antitumor composition, the hypericin, porphyrin, or analog is connected to the luciferin or analog, by way of a chemical tether or chemical linker. Thus, in a preferred embodiment of the invention, the first and second components of the antiviral or antitumor composition, i.e., the photosensitizing chemical and the energy emitting chemical, are connected by a chemical tether and form a tethered compound. As used herein, "chemical tether" or "chemical linker" is a chemical connector of two compounds.

The hypericin-luciferin tethered compound is preferably prepared through a condensation reaction of an activated hypericin with a luciferin analog. The luciferin analogs are synthesized from known compounds.

The compositions of the present invention also preferably contain a third component that contains chemical means for activating the transfer of energy or emission of light from the energy donating chemical. The chemical means of the present invention is preferably an activating chemical encoded by a gene under control of regulatory genetic elements. The DNA controlling the activating chemical operably contains regulatory motifs recognized by host cell transcription factors in addition to motifs recognized by viral regulatory proteins. As used herein, "regulatory element" ("regulatory nucleic acid sequence") is a region (sequence) that determines when, if, and at what level the DNA encoding the activating chemical is expressed. Such regulatory elements include promoters, enhancers, and transcription and translation initiation and termination sequences. As used herein, "nucleic acid sequence" refers generally to a polynucleotide molecule, more specifically to a linear series of nucleotides connected one to the other by phosphodiester bonds between the 3' and 5' carbons of the two adjacent pentoses.

Luciferin, a preferred energy donating molecule of the present invention, transfers energy or emits light when it reacts with the enzyme luciferase, ATP, and molecular oxygen, i.e., when the luciferase activates luciferin. Therefore, luciferase is an activating chemical when luciferin is the energy donating chemical. Thus, another preferred embodiment of the invention is regulating the expression of luciferase such that luciferase is preferentially or only expressed in virus-infected or tumor cells.

Regulating the activating chemical of an antiviral composition is preferably accomplished by first constructing an expression plasmid containing a gene encoding the activating chemical under control of a promoter. The DNA encoding the activating chemical is inserted into a vector, such as an expression plasmid, in proper orientation and correct reading frame for expression. Preferably, the antiviral composition is used to inactivate an enveloped virus but may be used for inactivating any viruses. More preferably, the antiviral composition is used to inactivate DNA enveloped viruses such as Herpes Simplex Virus and RNA enveloped viruses such as lentiviruses HIV and EIAV. The expression plasmid preferably contains a luciferase gene under control of an enveloped virus promoter, e.g., the retrovirus long terminal repeat (LTR). The promoter is selected such that replication of the virus will transactivate the promoter resulting in increased expression of luciferase leading to activation of luciferin and photoactivation of hypericin. Thus, photoactivation is localized to the virus-infected cells, thereby targeting the antiviral activity of the photosensitizing chemical.

The expression plasmid may be introduced into a cell by a variety of known methods including incorporation into a liposome. Other known methods that may be employed include, but are not limited to, the use of naked DNA transfer, microinjection, or calcium phosphate precipitation. A viral vector may also be constructed and introduced into a cell by viral mediated gene therapy or other known gene therapy techniques. Such a viral vector is preferably constructed by stably integrating a copy of the expression plasmid into a cell line. The viral vector is then produced from the cell line.

For use in an antitumor composition, the regulation of the activating chemical is also preferably accomplished by constructing an expression plasmid. The expression plasmid contains the gene encoding the activating chemical, e.g., luciferase, in an embodiment when luciferin is the energy donating chemical, under control of a promoter. The promoter is transactivated by elevated levels of proteins expressed in tumor cells. Transactivating the promoter increases expression of luciferase which activates luciferin and photoactivates the photosensitizing chemical, i.e., hypericin, in one embodiment. Thus, photoactivation is localized to the tumor cell, thereby targeting the antitumor activity of the photosensitizing chemical.

The expression plasmid used for regulating the activating chemical of the antitumor composition may be introduced into a cell by methods similar to those discussed for the antiviral composition. These methods include, but are not limited to, incorporation into a liposome, naked DNA transfer, microinjection, or calcium phosphate precipitation. A viral vector may also be constructed and introduced into a cell through known gene therapy techniques as discussed above.

The tethered compounds of the present invention are generally synthesized through a condensation reaction of the energy donating chemical with the photosensitizing chemical. In preferred embodiments of the present invention, the tethered compounds are synthesized by condensing a porphyrin, hypericin or their analogs with luciferin or its analogs.

Although luciferin is the presently preferred energy donating chemical, and hence luciferase the preferred activating chemical, there are various other chemical systems that produce sufficient energy or light to activate the photosensitizing chemical component of the compositions and methods of the invention. One particularly preferred energy donating chemical alternative to luciferin is dioxetane. Where dioxetane is the second component, i.e., the energy donating chemical, the chemical means (third component) for activating the transfer of energy or the emission of light is a "trigger" moiety attached to the dioxetane molecule but readily cleaved therefrom. Thus the activating chemical means of the invention need not be an expression plasmid. Depending on the virus or neoplastic cell to be targeted, the trigger may be, for example, a polypeptide that is cleaved by a protease produced by the virus or neoplastic cell. In addition, as will be shown in the detailed description which follows, the dioxetane itself preferably comprises a tethered compound, in which case the stable dioxetane contains both the photosensitizing chemical and the trigger. When the trigger is cleaved by the virus or neoplastic cell enzyme product or other targeted reagent, the dioxetane becomes unstable and produces an excited singlet, i.e., is activated, to activate the photosensitizing chemical moiety, which in turn inactivates the virus or kills the neoplastic cell.

The antiviral composition of the present invention may be used in a method for inactivating a virus. In a preferred method, the first and second components of the antiviral composition, preferably in the form of a tethered compound, are administered in pharmaceutically effective amount to the virus-infected cell. In addition, the third component of the antiviral composition, i.e., the component containing the chemical means for activating the transfer of energy or the emission of light, is also administered to the virus-infected cell, as discussed above, where it then activates the energy donating chemical which activates the photosensitizing chemical which inactivates the virus.

The antitumor composition of the present invention may be used in a method for treating tumors by destroying neoplastic cells. In a preferred method, the first and second components of the antitumor composition, preferably in the form of a tethered compound, are administered in a pharmaceutically effective amount to a neoplastic cell. In addition, the third component of the antitumor composition, i.e., the component containing the chemical means for activating the transfer of energy or the emission of light, is also administered to the neoplastic cell, as discussed above, where it then activates the energy donating chemical which then activates the photosensitizing chemical which destroys the neoplastic cell.

DETAILED DESCRIPTION OF THE INVENTION

Figure 1:
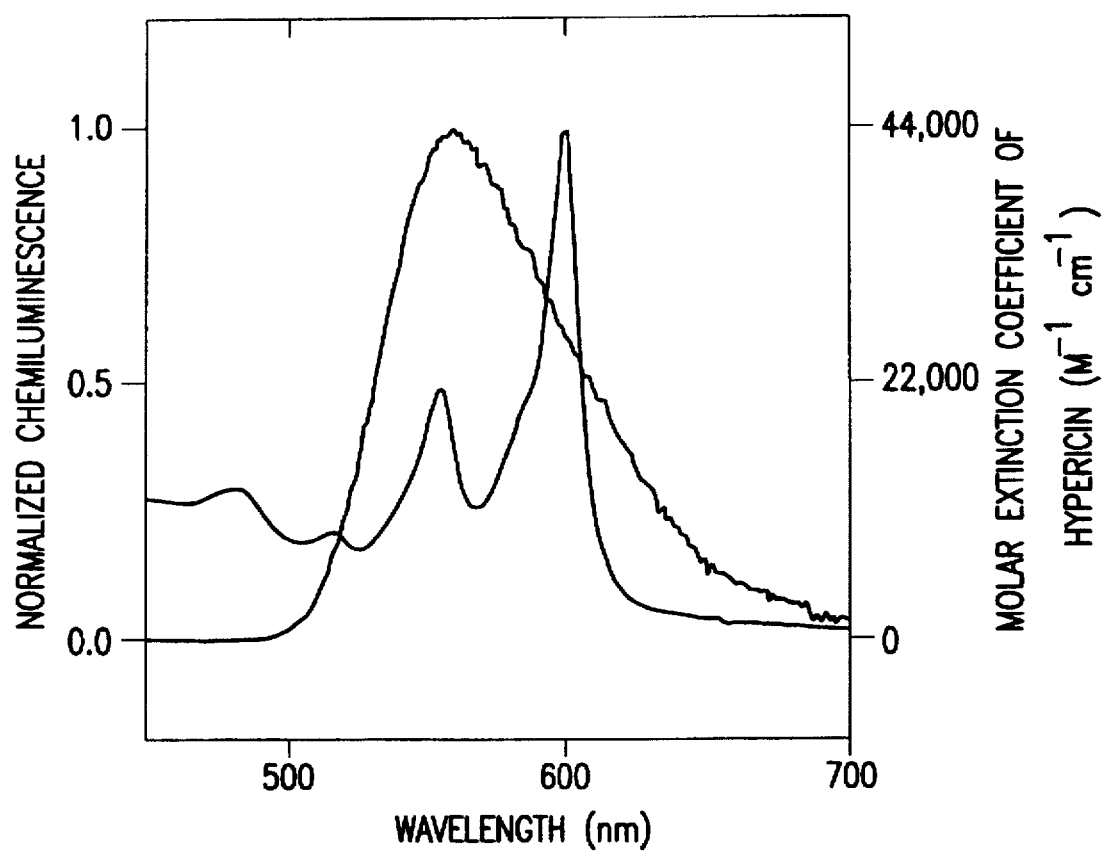
FIG. 1 is a graphic representation of the comparison of the chemiluminescent emission spectrum of the luciferase-catalyzed oxidation of luciferin and the absorption spectrum of hypericin in the red region of the visible spectrum.

Reference will now be made in detail to the presently preferred embodiments of the invention, which together with the following examples, serve to explain the principles of the invention.

The invention relates to antiviral and antitumor compositions comprising a first component containing a photosensitizing chemical, a second component containing an energy donating chemical, and preferably a third component containing means for regulating the emission of light or transfer of energy as well as to methods for synthesizing such components. The energy donating molecule should emit energy or light in a broad band of wavelengths in the range where the photoactive chemical absorbs. As used herein, a photosensitizing chemical is a chemical that is activated by light or energy transfer.

A preferable natural energy source is luciferin and its analogs. The reaction of luciferin with the enzyme luciferase, ATP, and molecular oxygen produces an intense long-lived emission from a triplet state, phosphorescence. The light produced by luciferin and its analogs is in the 520–680 nm region. Luciferin does not emit light or energy unless activated. Thus, regulating the expression of luciferase regulates the activation of luciferin.

The reaction of luciferin and luciferase provides luminescence reactions with the highest known quantum yields. However, various other energy donating chemicals provide significant quantum yields and may be used for activating the photosensitizing chemical according to the present invention. Such energy donating means, in addition to luciferin, include, but are not limited to, dioxetanes, dioxetanones, dioxetanediones and various other chemi- and bioluminescent compounds known in the art, for example, phthalhydrazide and compounds having oxygen—oxygen single bonds, such as hydroperoxides. See, e.g., Mayer and Neuenhofer, Angew. Chem. Int. Ed. Eng., 33, 1044–1072 (1994), which is incorporated herein by reference in its entirety. Of these luciferin alternatives, 1,2-dioxetane is currently the most preferred.

The photosensitizing chemical is preferably one selected from hypericin, other quinones, hematoporphyrin derivatives, phthalocyanins and porphyrins. A specific embodiment involves the use of hypericin as the photosensitizing chemical. Hypericin absorbs light in the 540–660 nm range. When hypericin is photoactivated, it produces singlet oxygen with a quantum yield of 0.74.

The energy transfer efficiency is optimized by connecting the energy donating chemical to a photosensitizing chemical by way of a chemical tether. The chemical tether connects the two ring compounds. Thus, a preferred embodiment of the invention includes the first and second components in the form of a tethered compound.

The tethering of the photosensitizing chemical and the energy donating chemical is directed to finding the most efficient energy transfer between the donor and the acceptor. The most efficient transfer depends on the relative separation and orientation of each of the two components.

Specifically, a preferred embodiment is directed to the connection between hypericin and luciferin or its analogs. Hypericin is a preferred photosensitizing chemical because low dosage administration of hypericin avoids undesirable side effects.

One embodiment of the invention is directed to the use of an activated hypericin analog, an anhyride or halide, for use as an intermediate in the preparation of the tethered compound. The anhyride and halide have the following formula:

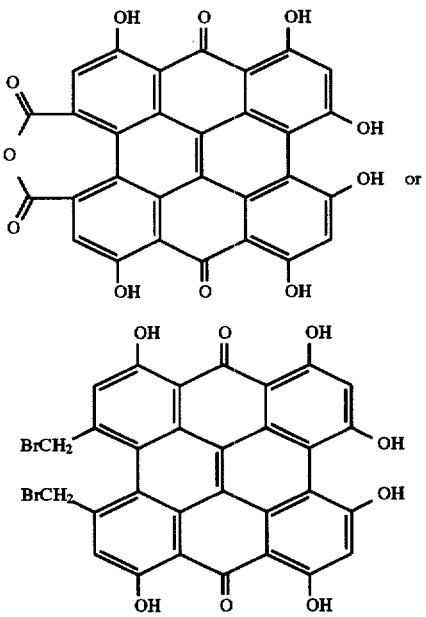

The anhyride can be prepared in three steps from hypericin. Acetylation of hypericin followed by chromic acid oxidation generates the diacid, which when reacted with DCC completes the synthesis of the anhydride. The halide is made by acetylation followed by benzylic halogenation.

Another embodiment of the invention is directed to using, as the photosensitizing chemical, porphyrins of the following formula:

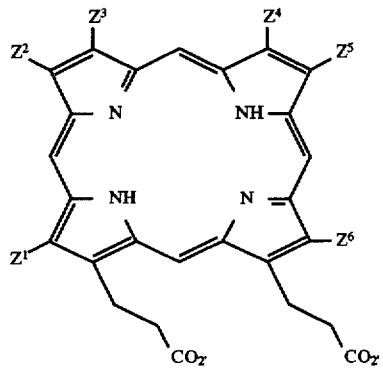

wherein $Z^1$-$Z^6$ are alkyl or alkenyl groups having 1–15 carbon atoms.

Luciferin and its analogs can be used to form tethered compounds with photoactive chemicals such as phorphyrins, hypericin, or other quinones. The tethered compounds must demonstrate overlap in the absorption spectra of the selected photoactive chemical with the emissions spectra of the energy donating chemical.

When oxidized, luciferin's broad emission band is centered at 560 nm and overlaps the two strongly absorbing bands of hypericin in the red region of the visible spectrum at 555 and 600 nm. See FIG. 1 for a comparison of the spectrum of the chemiluminescent emission of the luciferase-catalyzed oxidation of luciferin and the absorption spectrum of hypericin in the red region of the visible spectrum. This overlap allows for luciferin to be paired with hypericin.

Figure 2:
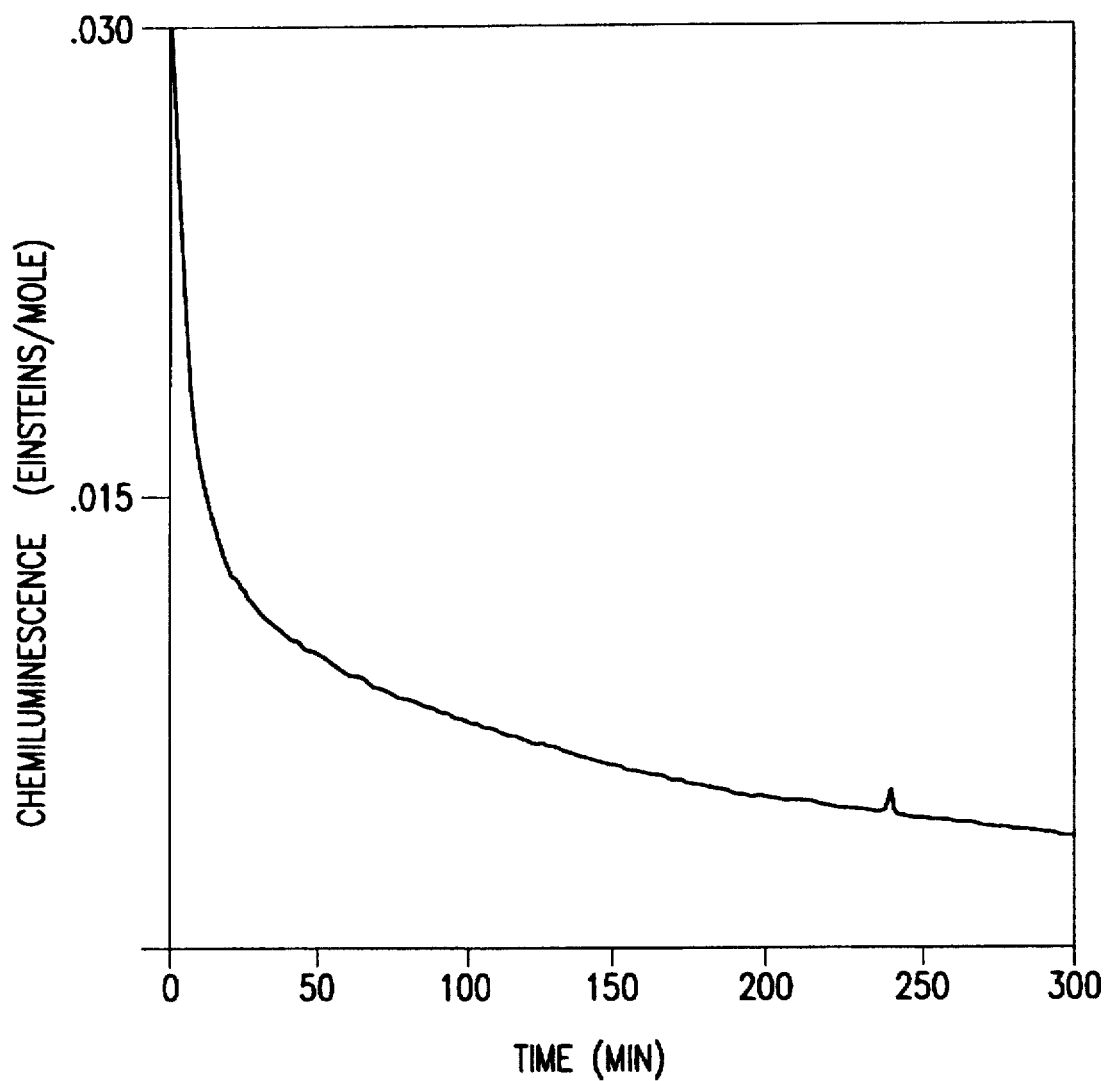
FIG. 2 is a graphic representation of the time course of the chemiluminescent emission from the luciferase-catalyzed oxidation of luciferin. The concentration of the reactants are as follows: [luciferase]=$2.67 \times 10^{-7}$M, [luciferin]=$1.18 \times 10^{-6}$M, [ATP]=$5 \times 10^{-5}$M; the buffer is 25 mM glycylglycine, 15 mM MgSO$_4$, 4 mM EGTA, 15 mM K$_3$PO$_4$ at pH=7.75 and the reaction is carried out at 25° C.

During the luciferase-catalyzed oxidation of luciferin, one photon of light is produced per molecule of substrate consumed. FIG. 2 presents the time course of the chemiluminesecent reaction of luciferin. The tethering of luciferin or its analogs must not disrupt the recognition and binding of the luciferin substrate by the enzyme for the light producing reaction, luciferase. Therefore, the preferred luciferin analogs for use in preparing tethered compounds are of the following formula:

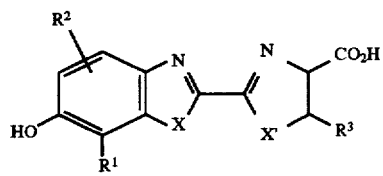

The tether or chemical linker is located at either $R_1$, $R_2$, $R_3$ or $R_4$. X and X' may be one of the following: S, O, H,H, CH=CH or $NR_4$. When $R_1$ is the site of the tether, $R_1$ is —$CO_2(CH_2)_nY$, wherein n is 2–15; Y is OH, SH or $NH_2$; and $R_2$–$R_4$ are H. When $R_2$ is the site of the tether, $R_2$ can be one of the following: —$(CH_2)_nCO_2H$ and —$S(CH_2)_nY$, wherein n is 1–15; Y is OH, SH or $NH_2$; and $R_1$ and $R_3$–$R_4$ are H. When $R_3$ is the site of the tether, $R_3$ can be one of the following: —$CO_2H$ and —$(CH_2)_nY$, wherein n is 1–15; Y is OH, SH or $NH_2$; and $R_1$–$R_2$ and $R_4$ are H. When $R_4$ is the site of the tether, $R_4$ is —$(CH_2)_nY$, wherein n is 2–15; Y is OH, SH or $NH_2$; and $R_1$–$R_3$ are H. The formula above displays luciferin when $R_1$–$R_3$ are H and both X and X' are both S.

Luciferin analogs may be synthesized in a number of ways, depending on which analog is to be used.

First, a benzothiazole intermediate is employed in the formation of a luciferin analog of the above-formula. The benzothiazole employed has the following formula:

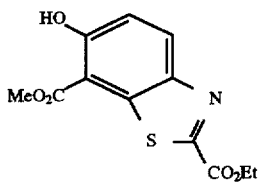

The benzothiazole is synthesized by adding hydrogen sulfide to an electron deficient imino quinone of the following formula:

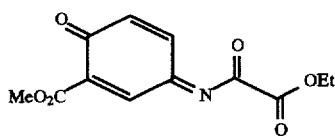

The resulting adduct undergoes dehydration to form the luciferin analog.

A second intermediate, a benzothiazole hydroxy nitrile has the following formula:

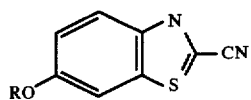

R is Me, H or PhCH$_2$. The benzothiazole hydroxy nitrile is formed by adding cyanide ion to a chloroalkoxybenzothiazole followed by dealkylation to form the benzothiazole nitrile.

Luciferin analogs are then synthesized by adding cysteine or a substituted cysteine to either one of the intermediates synthesized above.

Once the luciferin analogs are synthesized, these compounds are then reacted in a condensation reaction with the activated hypericin to form the tethered molecule of the following formula:

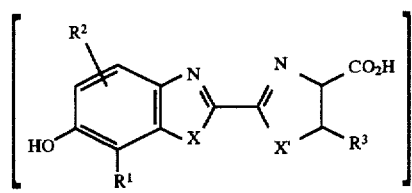

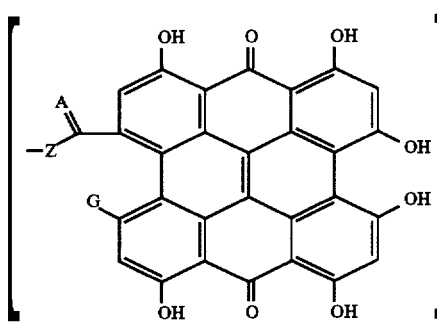

X and X' may be one of the following: S, O, H,H, CH=CH or NR$_4$. The tether or chemical linker of the tethered molecule occurs in one of four locations on the luciferin analog: R$_1$, R$_2$, R$_3$, or R$_4$. When the tether is located at R$_1$, the tethered compound has the following formula:

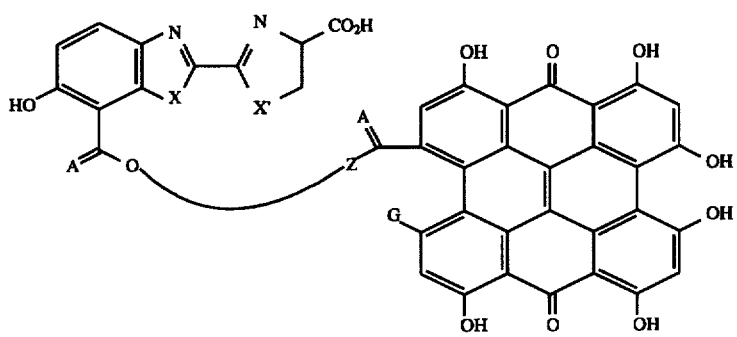

R$_1$ is —CO$_2$(CH$_2$)$_n$Z, wherein n is 2 to 15; and R$_2$-R$_4$ are H; Z is O, S or NH; A is O or H,H; and G is CH$_3$, CO$_2$H, CO$_2$Me, or CH$_2$Br.

If R$_2$ is the site of the tether, then the compound has the following formula:

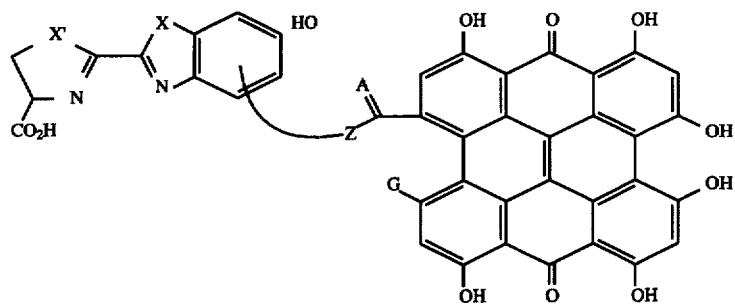

$R_2$ may be one of the following: —$(CH_2)_nCOZ$ and —$S(CH_2)_{n+1}Z$, wherein n is 1–15; $R_1$, $R_3$ and $R_4$ are H; Z is O, NH or S; A is O or H,H; and G is $CH_3$, $CO_2H$, $CO_2Me$, $CH_2Br$.

When $R_3$ is the site for the tether, the compound has the following formula:

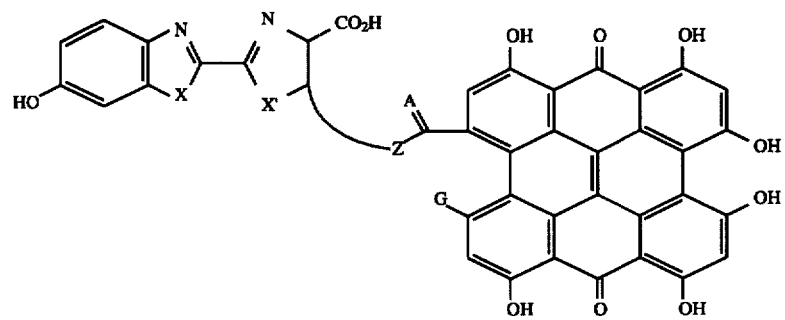

$R_3$ may be one of the following: —COZ and —$(CH_2)_nZ$, wherein n is 1–15; $R_1$–$R_2$ and $R_4$ are H; Z is O, NH, or S; A is O or H,H; and G is $CH_3$, $CO_2H$, $CO_2Me$, $CH_2Br$.

When $R_4$ is the site of the tether, the compound has the following formula:

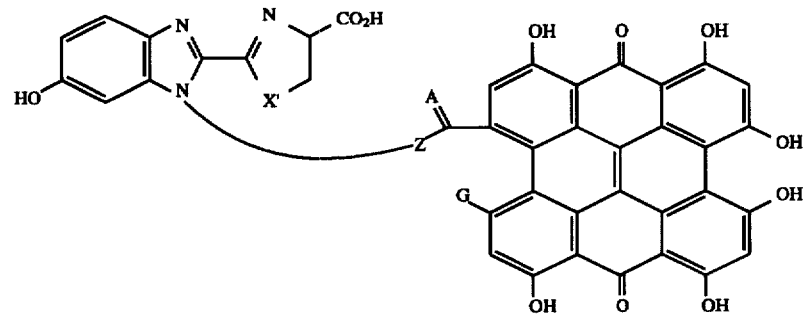

$R_4$ is —$(CH_2)_nZ$, wherein n is 2–15; $R_1$–$R_3$ are H; Z is O, NH, or S; A is O, or H,H; and G is $CH_3$, $CO_2H$, $CO_2Me$, $CH_2Br$.

The tethered compound may also contain the luciferin analogs discussed above linked to the porphyrin compound discussed above. As in the luciferin-hypericin tethered compound, the site of the tether or chemical linker may be at $R_1$, $R_2$, $R_3$ or $R_4$. The tether is attached to the porphyrin at either of its two carbonyls. The luciferin-porphyrin tethered compounds will be similar in structure to luciferin-hypericin tethered compounds except for the substitution of porphyrin for hypericin, i.e., the luciferin and tether or linker portion remain the same as those described above.

When the tethered compound contains a porphyrin instead of hypericin the compound has the following general formula:

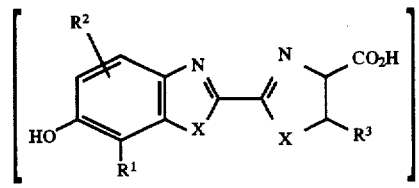

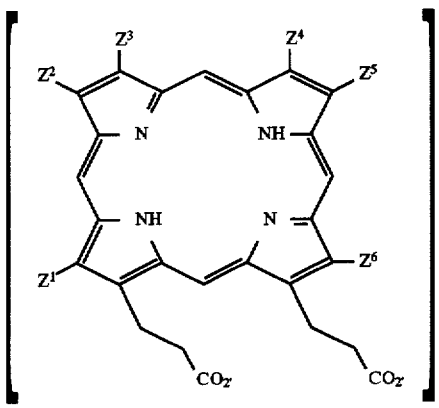

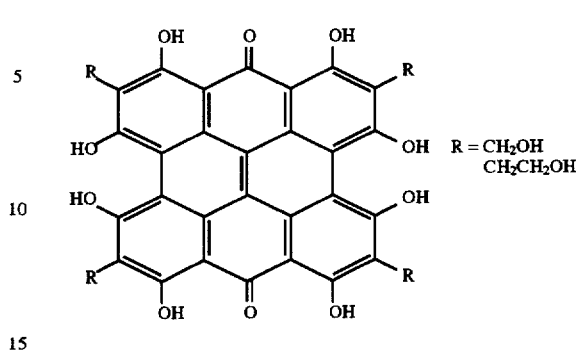

The tether is attached via $R_1$, $R_2$, $R_3$ or X (through $NR_4$) as explained and defined above. $Z^1$–$Z^6$ are each alkyl or alkenyl groups containing 1–15 carbon atoms.

One advantage of combining organic synthesis with virology and molecular biology is that organic compounds can be designed to exhibit enhanced physical properties, such as membrane permeability or polarity. As a consequence, delivery of these compounds can be targeted to subcellular organelles or to the cytoplasm. The tethered compounds of the invention are also synthesized by direct, high-yield synthetic routes. These synthetic routes are flexible, permitting the facile generation of various related compounds. Such compounds may be tested initially for photochemical properties, and promising molecules may then be further characterized biologically. Accordingly, this invention encompasses a broad range of tethered compounds that may be synthesized and tested by known techniques given the teachings of the present invention.

Particularly preferred tethered compounds are composed of luciferin or a luciferin analog and pseudohypericin (1) or its octahydroxy analog (2), shown below.

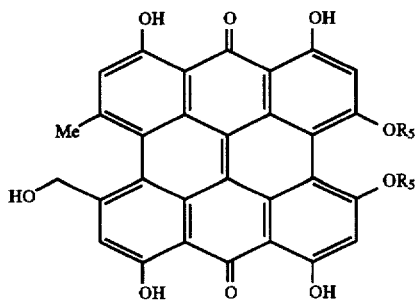

where $R_5$ is H or $CH_3$.

Particularly preferred tethered compounds are as follows:

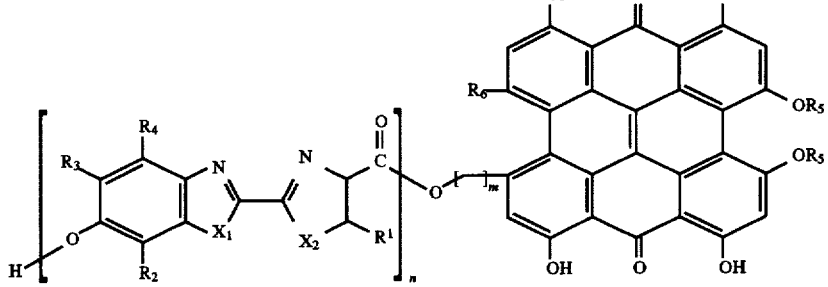

wherein $R_1$ is H, an alkyl or aryl; $R_2$ and $R_3$ are H, OH, Cl, CN or an alkyl; $R_4$ is H, OH, an alkyl or aryl, $R_5$ is H or $CH_3$ and $R_6$ is H, OH, Cl or an alkyl; $X_1$ is O, N-alkyl, N-aryl or S and $X_2$ is O, N-alkyl or S; and n is 1 to 10; and m is 1 to 4. Most preferably, $R_1$–$R_6$ are H and $X_1$ and $X_2$ are S.

In addition, two general types of tethered compounds may be prepared. One type uses a "caged" luciferin wherein the carboxylic acid group present in luciferin is capped as an activated ester. This ester form of luciferin will not react with luciferase until it is cleaved by esterases within the cell. This type of tethered compound exhibits enhanced membrane permeability and is cleaved rapidly by esterases present in cells. Preferred tethered molecules of this type are shown below (3a–3c). Compound 3c contains four molecules of luciferin per molecule of the hypericin analog. This is significant since once the luciferin interacts with luciferase, it is transformed into a different compound which can no longer function as a substrate for luciferase. The hypericin analog, on the other hand, is a catalyst in this reaction. Alternatively, a compound can be prepared as shown above wherein up to 10 or more luciferin molecules are linked together at the CO₂H and OH ends to form a luciferin chain. In such a chain, n is preferably from 1 to 10.

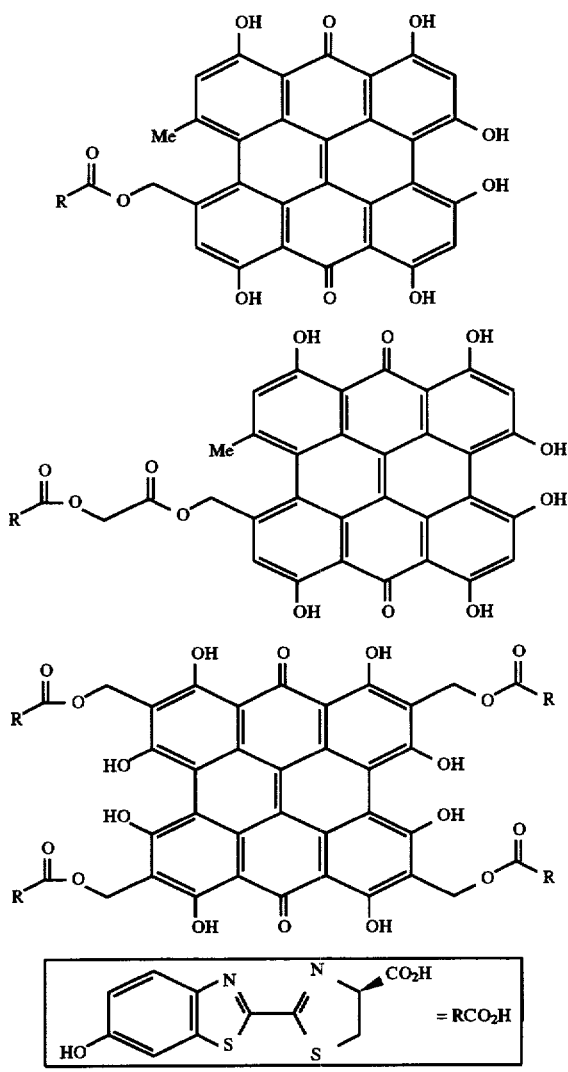

Tethered compound 3a may be prepared from commercially available (e.g., CalBiochem) pseudohypericin (1) and luciferin using isobutyl chloroformate as a catalyst. Tethered compound 3b is made using pseudohypericin, bromoacetic anhydride and luciferin, by first reacting pseudohypericin with bromoacetic anhydride to generate a bromo ester which will readily react with the triethylammonium salt of luciferin to form 3b. Tethered compound 3c is prepared from quinone 2 (R=CH₂OH) and four molecules of luciferin. Quinone 2 is prepared in three steps from 2,6-dichlorobenzoquinone and 2-methyl ethyl acetoacetate. A water-soluble carbodiimide reagent mediates the reaction between quinone 2 and luciferin. A related compound with two methylene groups between the aromatic ring and the luciferin subunit can also be readily prepared.

A second type of particularly preferred tethered compound may be generated by combining a "non-caged" analog of luciferin with 1 or 2. These tethered compounds are not cleaved by esterases, and remain chemically linked when added to cells. This enables very efficient intramolecular energy transfer between hypericin and the chemiluminescent intermediate of the reaction of luciferin with luciferase.

We have also developed a particularly preferred enantiospecific synthesis of luciferin. The major advantage of our synthesis is the convenient synthesis of luciferin in multigram quantities from inexpensive (less than $1/gram) precursors. Additionally, this route allows direct access to amino analogs of luciferin. This is significant, since various amino analogs of luciferin, for example the analog depicted below, react with luciferase.

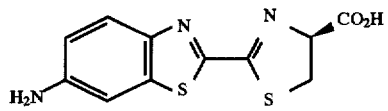

The preferred route for synthesis of the preferred luciferin analogs (4a–4d) is shown below. Compounds 4a and 4b are prepared from an intermediate, the benzothiazolehydroxy nitrile second intermediate shown above, in the synthesis of luciferin. Formation of the allyl ether, Claisen rearrangement and hydroboration are standard organic reactions. The reaction of the nitrile moiety with cysteine has precedent from the White et al., *J. Am. Chem. Soc.*, 83, 2402 (1961), synthesis and from our synthesis of luciferin.

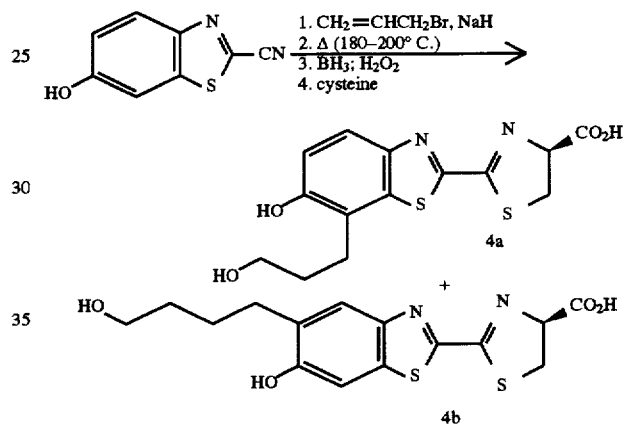

Luciferin analog 4c is prepared in three steps from an early intermediate in the synthesis of luciferin as shown below. The chloride is converted into a nitrile and a cystein unit is introduced. Alkylation of an amine with bromoethanol is a standard reaction.

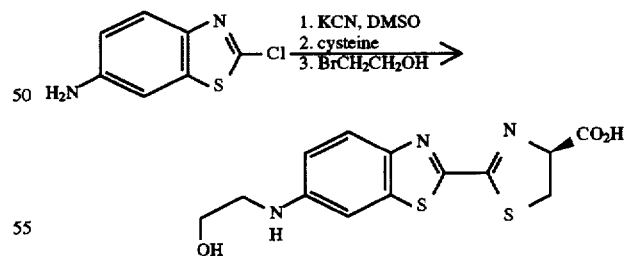

Luciferin analog 4d is prepared as shown below. Nucleophilic addition to isothiocyanates (R-NCS) followed by alkylation of the resulting intermediate on sulfur with an electrophile is a well-established reaction sequence.

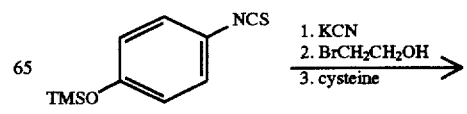

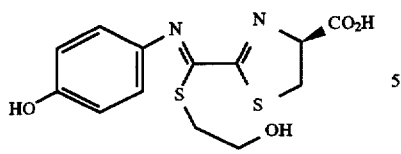
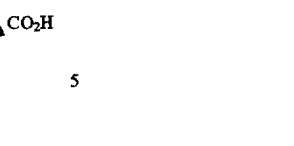
Connection of the luciferin analogs with pseudohypericin, quinone 1, results in the series of particularly preferred "non-caged" tethered compounds, 5a–5d, shown below.
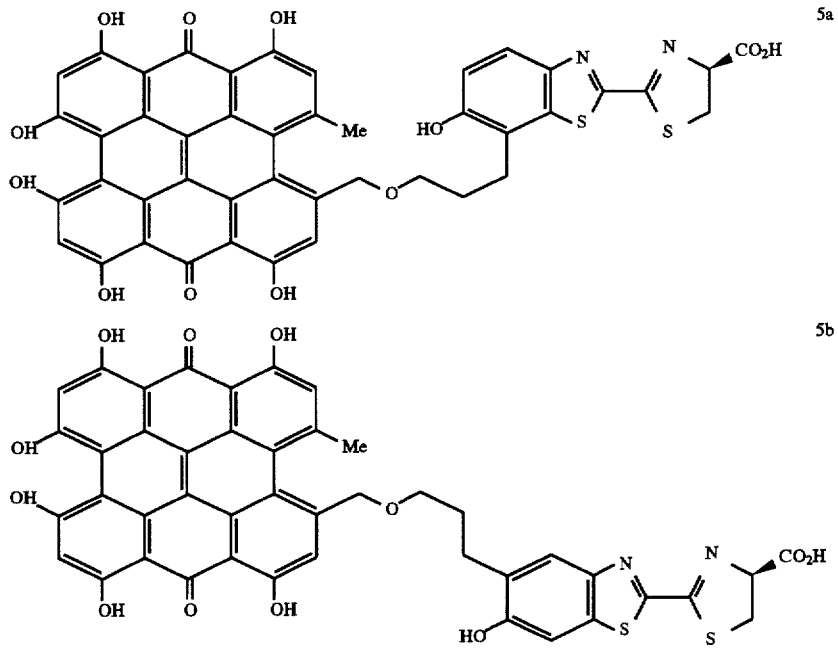
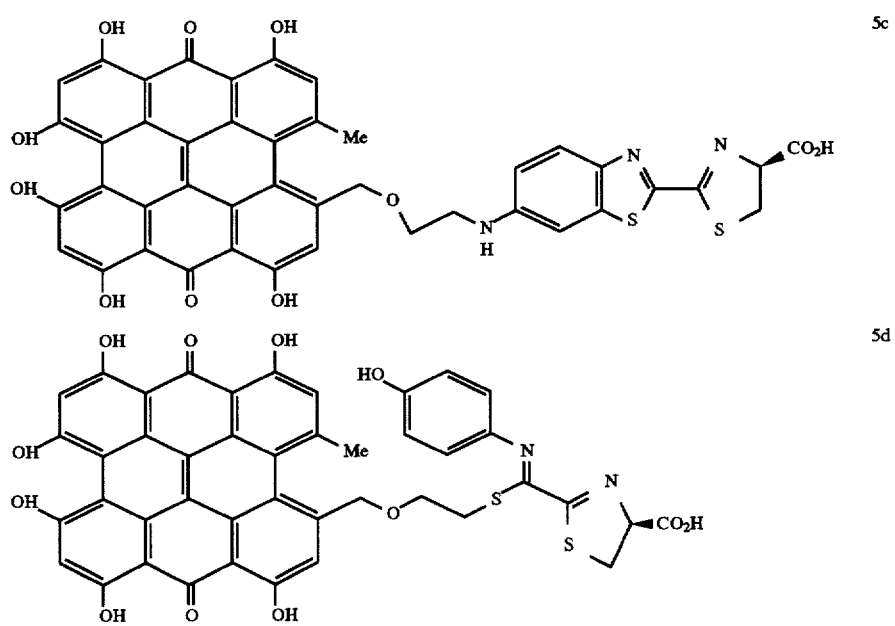

There are a number of analogs of luciferin that react with luciferase, including the amino analog and other analogs mentioned above. The analogs shown below are also substrates for luciferase. The structural requirements for effective substrates are relatively broad, and other analogs may be prepared by known techniques given the teachings herein.

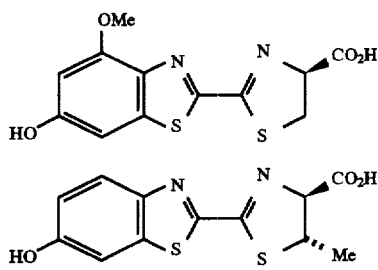

The tethered compounds of the present invention can contain any combination of photosensitizing chemicals and energy donating chemicals linked by a tether, providing that the energy donating molecule activates the photosensitizing molecule in sufficient degree to obtain antiviral or antitumor activity. Tether selection is based on (1) the rate of transfer from the donor to acceptor and (2) the recognition of the substrate by the catalyst for the light producing reaction. The rate and quantum yield of the enzyme catalyzed reaction may be monitored in order to screen for the potential effects of inhibition of reactivity.

A preferred example of a non-luciferin energy donating chemical is 1,2-dioxetane. Dioxetane can also readily be used to form a tethered compound, as described in more detail below and in the examples which follow. The resulting stable dioxetane molecule contains both the light acceptor and the trigger to create the light. One advantage of this system is that it does not require oxygen and thus can be used in hypoxic cells. Another particularly advantageous aspect of the dioxetane system embodiments of the invention is that, since the dioxetane molecule also includes a trigger moiety (component three) the dioxetane includes all three components of the invention, and thus, it can be used to inactivate a virus or kill a neoplastic cell by administering to the patient a single capsule, injection, or other form of administration.

Any compound bearing a four-membered ring containing two oxygen atoms is a "dioxetane." The structure shown below is a 1,2-dioxetane.

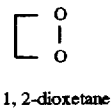

1, 2-dioxetane

Because of the ring strain of the four-membered ring and the weak oxygen—oxygen bond, the dioxetane is a labile molecule. For that reason, most stable dioxetanes have bulky substituents which hinder attack by nucleophiles. Dioxetanes can be opened either by nucleophilic attack or by electron transfer. Steric hindrance from bulky substituents does not significantly affect electron transfer.

Below is illustrated a preferred stable dioxetane A. R is an alkyl group which contains the moiety, i.e., photosensitizing chemical, which will accept the light produced and thus inactivate the virus or neoplastic cell when the dioxetane breaks. The dioxetanes according to the invention may contain any of the aforementioned preferred photosensitizing chemicals or other photoactive chemicals useful for PDT. The presently preferred photosensitizing moieties for the dioxetane are the hypericins and protoporphyrins, with the halide analog of hypericin being most preferred.

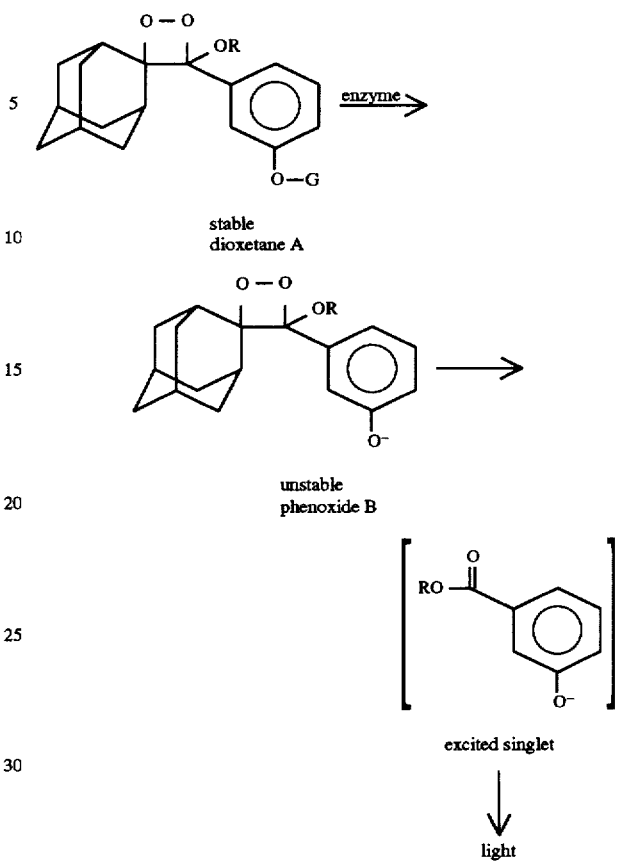

In cases where the above-illustrated R does not contain the light-accepting moiety, then this is a short chain alkyl group ($C_1$–$C_7$), for example, as shown below. The group G is the "trigger" which reacts with a reagent, preferably an enzyme, to generate the unstable phenoxide B. For example, if G is a carbohydrate such as galactose, then the enzyme beta-galactosidase can be used to cleave the O—G bond. If G is a phosphoric acid derivative or an attendant ester, then a suitable reagent would be an alkaline phosphatase. Most preferably, G is a polypeptide chain corresponding to a sequence cleavable by an HIV protease, thus targeting the dioxetane-activation of the photosensitizing chemical to HIV infected cells. The reagent may also be a strong base, a fluoride ion or any reagent that cleaves the trigger group G to activate the dioxetane. Once the phenoxide B is created, it undergoes internal electron transfer with the dioxetane to produce an excited-state species which cleaves to give an excited singlet (shown above) which reacts with the light-accepting moiety. The light-accepting moiety can also be located on G, as shown below.

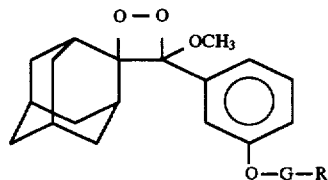

Viruses generally encode one or more proteases which function to cleave viral polyproteins during viral replication. The dioxetane tether is suitably targeted to virus-infected cells if the trigger G is a small chain of synthetic peptides which comprise the cleavage site for a given viral protease. For example, the cleavage site of retroviral proteases are variable, but they share common features, including the presence of hydrophobic residues on either side of the cleavage site, with some preference to Tyr or Phe preceding the cut, and Pro following the cut. Specific synthetic peptide sequences shown to be cleaved by HIV-1 protease are presented in Goobar-Larsson et al., *Virology*, 206, 387–394 (1995), which is incorporated by reference herein in its entirety. Additional proteases which target viral proteins include the Kex2p endoprotease which cleaves the HIV-1 gp 160 (Moulard et al., *Biochimie*, 76(3–4), 251-6 (1994) and Moulard et al., *Eur. J. Biochem.*, 225(2), 565-72 (1994), which are incorporated by reference herein in their entirety).

The dioxetane tether may also be cleaved by proteases expressed at high levels in tumor cells. Membrane-bound and secreted proteases are found in many transformed cells where they are thought to play a role in mitogenesis and metastasis. These include fibronectin-degrading proteases (Chen and Chen, *Cell*, 48, 193–203 (1987), which is incorporated by reference herein in its entirety) and plasminogen activators, serine proteases, and collagenases (Dano et al., "Plasminogen Activators, Tissue Degredation, and Cancer," *Advances in Cancer Res.*, Vol. 44, 139–164 (1985), which is incorporated by reference herein in its entirety).

When used for treating virus infections such as DNA or RNA enveloped virus infections, the first and second components of the antiviral composition, preferably in the form of a tethered compound, may be administered orally, parenterally, and preferably intravenously. In any event, a pharmaceutically effective amount of the compound is administered. An effective amount is determinable by persons skilled in the art in the view of teachings disclosed herein.

Further, the first and second components, preferably in the form of a tethered compound, can be used at dosages containing from about 0.001 micrograms to about 100,000 micrograms per kilogram body weight per treatment, preferably between about 1 microgram and about $5 \times 10^4$ micrograms per kilogram of body weight per treatment.

The duration and number of doses or treatments required to control a particular virus will vary from subject to subject, depending upon the severity and stage of the illness and the subject's general condition and will also depend on the activating chemical, as well as the toxicity (if any) of the tethered compound. This will be determinable by persons skilled in the art in view of the teachings contained herein. The total dose required for each treatment may be administered in divided doses or in a single dose. The preferred form of the first and second components, i.e., the tethered compound, may be administered daily, more than once daily, one or two times a week, or as determined by the subject's condition and the stage of the disease.

Those skilled in the art will appreciate that the frequency of treatment is subject to optimization, which can be determined by routine experimentation according to methods well known in the art, e.g., by establishing a matrix of dosage and frequency and assigning a group of experimental subjects to each point of the matrix. Design of this experiment will preferably take into account the tissue accumulation properties of the compounds of the present invention.

The present invention also provides pharmaceutical compositions and formulations for treating lentiviral infections. The first and second components, preferably in the form of a tethered compound, can be incorporated in conventional, solid and liquid pharmaceutical formulations (e.g. tablets, capsules, caplets, injectable and orally administrable solutions) for use in treating mammals that are afflicted with viral infections. The pharmaceutical formulations of the invention comprise an effective amount of the tethered compounds of the present invention as the active ingredients. For example, a parenteral therapeutic composition may comprise a sterile isotonic saline solution containing between about 0.001 micrograms and about 100,000 micrograms of the tethered compounds of the present invention as described above. It will be appreciated that the unit content of active ingredients contained in an individual dose of each dosage form need not in itself constitute an effective amount since the necessary effective amount can be reached by administration of a plurality of capsules, tablets, injections or combinations thereof.

Each formulation according to the present invention may additionally comprise inert constituents, including pharmaceutically-acceptable carriers, diluents, fillers, salts, and other materials well-known in the art. Selection will depend upon the dosage form utilized and the particular purpose to be achieved according to the determination of the ordinarily skilled artisan in the field. For example, tablets may be formulated in accordance with conventional procedures employing solid carriers well known in the art. Examples of solid carriers include, starch, sugar, bentonite, silica and other commonly used carriers. Propylene glycol, benzyl alcohol, isopropanol, ethanol, dimethylsulfoxide (DMSO) dimethylacetamide or other biologically acceptable organic solvents or aqueous solutions (e.g. water with a pH higher than 7 and preferably about 8) may be used as diluents, carriers or solvents in the preparation of solid and liquid pharmaceutical formulations containing the anti-lentiviral compositions of the present invention. Further nonlimiting examples of carriers and diluents include carbohydrates, albumin and/or other plasma protein components such as low density lipoproteins, high density lipoproteins and the lipids with which these serum proteins are associated. Such lipids include phosphatidyl choline, phosphatidyl serine, phosphatidyl ethanolamine and neutral lipids such as triglycerides. Additional lipid carriers include without limitation tocopherol, retinoic acid and cyclodextranes. Semisolid formulations such as those well-known in the art (e.g. suppositories) are also contemplated.

Preferred parenteral dosage forms may comprise, for example, an isotonic saline solution, containing between about 0.1 micrograms to about 100,000 micrograms of the tethered compounds of the present invention.

Capsules employed in the present invention may be made from any pharmaceutically acceptable material, such as gelatin or cellulose derivatives. Sustained release oral and transdermal delivery systems are also contemplated, as is interveneous injection.

The antiviral and antitumor compositions containing the preferred luciferin-hypericin tethered molecule require luciferase for the catalysis of the light producing reaction and the activation of hypericin. The activation of the light source is regulated such that the hypericin is photoactivated where needed. The regulation of luciferin activation is achieved by regulating the expression of luciferase. The antiviral or antitumor compositions containing the preferred dioxetane compound require a reagent to trigger the dioxetane. The trigger preferably is a polypeptide that is cleaved by a viral or neoplastic protease inside the virus infected or tumor cell, thus targeting production of the excited singlet and activation of the hypericin or other photosensitizing chemical to the infected or tumor cells.

The third component of the antiviral composition, i.e., the component containing the chemical means for activating the transfer of energy, preferably regulates the expression of the activating chemical. In a preferred antiviral composition, the activating chemical is luciferase, which is regulated by placing the gene encoding luciferase under control of a promoter that is transactivated by replication of the virus. By placing the expression of luciferase under control of such a promoter, replication of the virus transactivates the viral promoter resulting in an increased expression of luciferase leading to activation of luciferin and the photoactivation of hypericin. These events are localized in virus-infected cells thereby targeting the antiviral activity of hypericin.

Specifically, the expression of luciferase is targeted to the virus-infected cells by constructing an expression plasmid which contains the gene coding for luciferase under control of a promoter that is transactivated by repliction of said virus. Examples of such promoters include HIV TAR, the sequence of which is incorporated herein by reference and which is described in Berkhout et al., Cell, 59: 273-282 (1989); Berkhout et al., Cell, 62: 757-767 (1990) and Berkhout et al., J. Virol., 66: 139-149 (1992), all of which are incorporated herein by reference, or the consensus enhancer sequence present in the promoter of Herpes Simplex Virus alpha genes, the sequence of which is incorporated herein by reference, and which is described in Fields et al., Virology, Second Ed. 1990, and Mackem et al. J. Virol, 44: 939-949 (1982) each of which is incorporated herein by reference, and the EIAV long terminal repeat (LTR), the sequence of which is incorporated herein by reference, and which is shown in FIG. 1 of Carpenter et al., J. Virol., 65(3), 1605-1610 (1991), which is incorporated herein by reference.

Figure 3A:
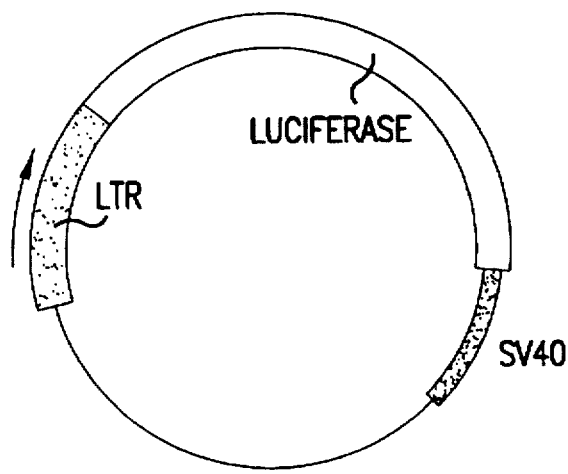
FIG. 3A is a representation of an expression plasmid containing the luciferase gene under the control of the EIAV LTR.
Figure 3B:
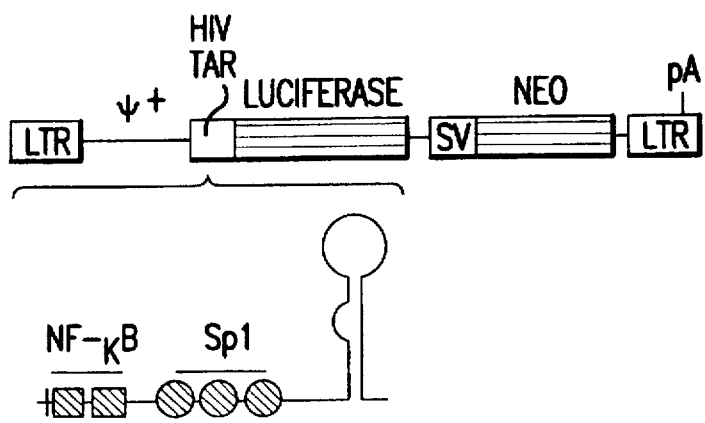
FIG. 3B is a representation of a retroviral vector containing the luciferase gene under the control of the HIV LTR. This vector may be used for killing HIV/HIV-infected cells.

FIG. 3A shows a representation of the expression plasmid containing the luciferase gene under control of the EIAV MA-1 LTR. The plasmid containing the EIAV LTR is transfected into Cf2th cells and there expresses luciferase in the presence of either EIAV or the viral transactivating protein, Tat, but not in normal Cf2th cells. In one embodiment, the plasmid is first placed into a liposome before it is directly transfected into cells. Similar constructs containing, for example (FIG. 3B), HIV LTR in place of EIAV LTR express luciferase in the presence of HIV or HIV Tat. Such HIV constructs can use various different promotor sequences, provided that at least one or more Tat-responsive cis-acting sequences are included within each promotor sequence controlling luciferase expression. See, e.g., Buchschacher et al., "Human Immunodeficiency Virus Vectors for Inducible Expression of Foreign Genes," J. Virol., 66:5 pp. 2731-2739 (1992) and Buchschacher, "Molecular Targets of Gene Transfer Therapy for HIV Infection," JAMA, 269:22, pp. 2880-2886 (1993), each of which is incorporated by reference herein in its entirety.

Any method of introducing DNA into a cell is sufficient for the gene transfer and therapy herein described. Methods for transferring DNA into cells include, but are not limited to, the use of viral vectors, microinjection, liposome mediated, calcium phosphate precipitation and simple naked DNA transfer. See Lim et al., Molec. and Cel. Bio., 7(10): 3459-3465 (1987); Kasid et al., PNAS, 87: 473-477 (1990); Gilboa, Eli, Retrovirus and Disease, Academic Press, Inc. pp. 95-111 (1989); Kantoff et al, PNAS 83: 6563-6567 (1986); Kasid et al., PNAS, 87: 473-477 (1990); Kantoff et al., J. Exp. Med, 166: 219-234 (1987); Cornetta et al., J. Virol. Meth., 23: 187-194 (1989); and Culver et al., PNAS, 88: 3155-3159 (1991). The disclosure of each of these articles is incorporated herein by reference.

The third component of the antiviral composition, i.e., the component containing the means for activating the transfer of energy, is preferably introduced into patients through gene therapy techniques. In one embodiment, the therapy involves retroviral mediated gene therapy that includes construction of a retroviral vector in which the DNA encoding the activating chemical, e.g., luciferase, is placed under the control of a modified retroviral promoter which is activated in virus-infected cells. In one embodiment, the therapy involves first constructing a plasmid vector containing a retroviral LTR, retroviral packaging sequences, and the DNA encoding luciferase. Additionally, the vector may contain DNA encoding a selectable marker, e.g., neomycin resistance.

The plasmid is introduced into a eukaryotic cell or cell line, preferably a packaging cell, which harbors stably integrated proviral sequences sufficient for expression of retroviral structural proteins, but which are deficient in sequences required for packaging and replication of RNA transcribed by proviral DNA. Following introduction of the plasmid vector, cells containing stably integrated plasmid DNA are identified by expression of the selectable marker. Encapsidation of vector sequences by the proviral structural proteins results in production of retrovirus particles which contain genetic material encoding the activating chemical under the control of a regulated promoter. Transfected cells which produce such retrovirus particles are referred to as producer cells, and the virus particle produced from these cells is referred to as the retrovirus vector.

The vector may be introduced into human and mammalian cells in a variety of methods. One method comprises removing cells, e.g., lymph cells from the patients infected with the virus to be inactivated. The removed cells are then infected with the constructed viral vectors or by other means of introducing DNA such as liposome mediated transfer. If the DNA is introduced by liposome mediated transfer, the liposome contains plasmid DNA containing the promoter controlling expression of the activating chemical, the activating chemical and in some embodiments, a selectable marker. The patient cells containing the gene encoding the activating chemical are selected through the use of the selectable marker, i.e., cells are selected if they demonstrate neomycin resistance. The selected cells are then grown and reintroduced into the patient.

Alternatively, the producer cell lines, constructed as described above, are introduced directly into the patient, resulting in infection in vivo. Further, it is possible to introduce the vectors directly into the patient.

In each of the above-described embodiments, the DNA encoding the activating chemical is preferably stably integrated within the patient's cell. Expression of the activating chemical is regulated, such that only virus-infected cells express high levels of the activating chemical. The frequency of administering the third component via gene therapy or other known techniques will depend on how long the inserted DNA can be expressed and how long the cells containing the inserted DNA will survive.

In one specific embodiment of the invention, the tethered compound is used to inactivate HIV, an RNA lentivirus. The tethered compound comprises hypericin and a luciferin analog, the first and second components, and is administered as discussed herein. The third component is administered by constructing a viral vector containing (1) a promoter that contains HIV TAR and upsteam NF-kB and SP-1 sites, or sequences necessary for TAT-mediated transactivation, (2) the packaging sequences, (3) the luciferase gene and (4) Neo$^r$, a neomycin resistance marker. The packaging cell line includes a provirus expressing HIV env/gp 120 to target CD4 positive cells in which HIV replicates, and no packaging sequence. The resultant virus vector line is infected into patient cells either in vivo or ex vivo. Once the genetic material is integrated into the patient's cells, luciferase is expressed to high levels only in HIV infected cells. The expressed luciferase activates the luciferin analog of the administered tethered compound. The luciferin analog in turn activates the photosensitizing chemical of the administered tethered compound. The photosensitizing chemical, once activated by the luciferin analog, inactivates HIV.

Figure 3C:
FIG. 3C shows the construct of a retroviral vector for cell-specific killing of melanoma cells.

The means for regulating the activating chemical in the preferred embodiment are not the same when the composition is used to destroy tumor cells. Specifically, the third component of an antitumor composition containing DNA encoding an activating chemical is also located on an expression plasmid. The DNA, however, is under control of a different promoter, such as the carcino-embryonic-antigen (CEA) promoter. Increased expression of the activating chemical occurs when levels of certain proteins, e.g., CEA protein, are elevated. Thus, the promoter is activated by levels of certain proteins that are elevated only in tumor cells. Therefore, the expression of the activating chemical, i.e., luciferase, is localized to the tumor cells. Other promotors useful for targeting photoactivated tumor cell destruction according to the invention include, but are not limited to, the tissue-specific tyrosinase promoter (see FIG. 3C and Example 10).

Gene transfer into tumor cells occurs through methods as those described herein for transfer into virus-infected cells, i.e., via the use of known methods such as viral vectors, liposome mediated transfer, microinjection and naked DNA transfer.

The invention also provides a method for destroying noeplastic cells, preferably malignant cells. Thus, it can be used to treat tumors, preferably cancers. The method for destroying a neoplastic cell is similar to that of inactivating a virus in that the photosensitizing chemical (component one) and the energy donating chemical (component two), preferably in the form of a tethered compound, are introduced into the tumor cell along with the means for activating the energy donating chemical (component three). However, in this embodiment, elevated levels of certain proteins present in tumor cells increases expression of the activating chemical, which then activates the energy donating chemical, which photoactivates the photosensitizing chemical, resulting in destruction of the tumor cell. Expression of the activating chemical may be regulated by various means as discussed above.

It is to be understood that the application of the teachings of the present invention to a specific problem or environment will be within the capabilities of one having ordinary skill in the art in light of the teachings contained herein. Examples of the compounds and compositions of the present invention and methods of their preparation and use appear in the following examples.

EXAMPLE 1

Preliminary Testing of an Antiviral Composition Containing Hypericin and Luciferin Initially, hypericin and luciferin/luciferase (commercially available) were mixed under aerobic conditions in the dark in the presence of EIAV according to the following protocol:

Materials and Methods

Serial ten-fold dilutions of EIAV in Hank's balanced salt solution were mixed with an equal volume of luciferase assay buffer containing 25 mM glycylglycine, pH 7.8, 15 mM $MgSO_4$, 4 mM EGTA, 150 mM $KPO_4$, 2 mM ATP, and 1 mM DTT. Luciferin and luciferase were added to final concentrations of 0.4 mM and $1.6 \times 10^{-7}$ M, respectively. The reactions were incubated in the dark for 45 min, and ten-fold serial dilutions were inoculated onto $10^6$ ED cells in the presence of polybrene. Cells were incubated 5 days at 37° C., fixed in 100% methanol and stained for the presence of EIAV as previously described (Carpenter et al., *J. Virol*, 65(3): 1605–1610 (1991), incorporated in its entirety herein by reference). Foci of EIAV-infected cells were quantitated and the results expressed as focus-forming units per ml (FFU/ML).

Results

Figure 4:
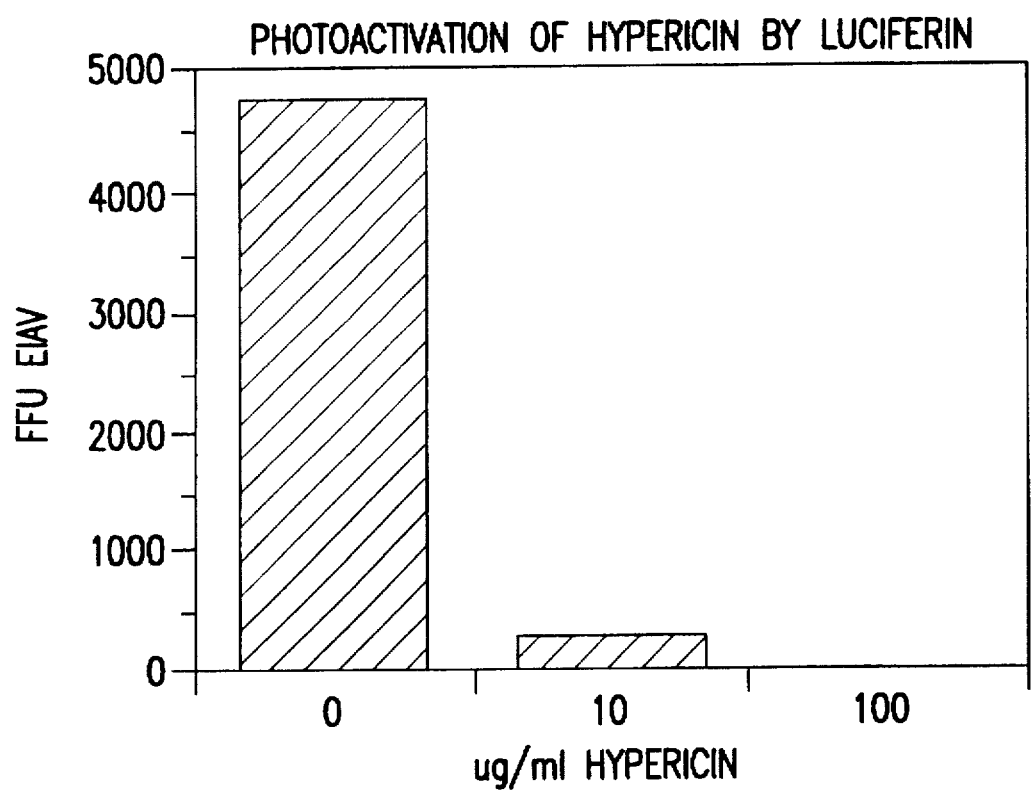
FIG. 4 shows the antiviral activity of hypericin in the presence of luciferin and luciferase.

Hypericin activation by chemiluminescence was dependent on the concentration of hypericin (FIG. 4). Approximately 90% reduction in virus production was observed with 10 μg/ml hypericin. The antiviral activity of hypericin was not as efficient as what we previously observed using white light (Carpenter and Kraus, *Photochem and Photobio.*, 53(2): 169–174 (1991) incorporated in its entirety herein by reference). However, the results demonstrate that the luciferase-catalyzed luciferin reaction photoactivates hypericin in vitro.

EXAMPLE 2

Synthesis of Hypericin Analogs for Use in Preparing Tethered Compounds

Analog A—Hypericin Anhydride

To a stirred suspension of the diacid formed by acetylation of hypericin followed by chromic acid oxidation, (H. J. Banks et al. Aust. J. Chem., 1976,29,1509) in ether-chloroform at 0° C. was added dicyclohexyl-carbodiimide (1.3 eq). The suspension was allowed to slowly warm to RT over one day. A precipitate was filtered. The filtrate was concentrated to give the anhydride (unstable) which was immediately reacted with the luciferin analogs synthesized as described in the examples below.

Analog B—Bisanthraquinone

A solution of bianthraqunoyl (50 mg, 0.088 mmol) in 14 ml of $AcOH/CH_2Cl_2$ (1:1) was cooled to 0° C. Then a solution of $Pb(OAc)_4$ (117 mg, 0.26 mmol) in 6 ml of $AcOH/CH_2Cl_2$ (1:1) was added dropwise at 0° C. The mixture was stirred at 0° C. for 2 hours and was poured into 2N HCl (100 ml). Then the mixture was extracted with AcOEt (30 ml×3), washed with $H_2O$, dried over $Na_2SO_4$. After the solvent was removed under reduced pressure, the residue was purified by flash chromatography on silica gel eluted with Hexane/AcOEt (2:1), AcOEt/EtOH (9:1) to provide bisanthraquinone 39 mg (78%).

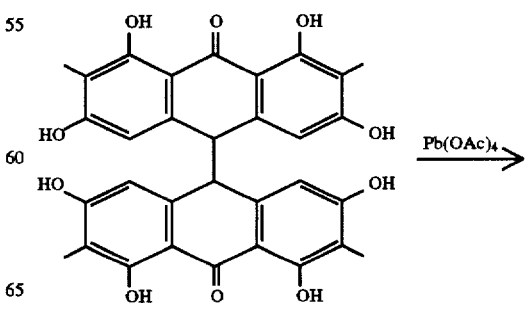

27

-continued

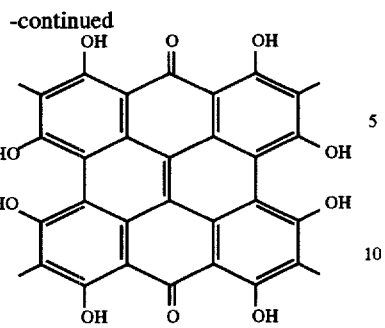

Analog C—Bianthraqunoyl

A solution of anthrone (500 mg, 1.75 mmol) in 15 ml EtOH was heated to reflux. Then a solution of FeCl₃(H₂O)₆ (550 mg, 2 mmol) in 30 ml of EtOH was added dropwise over 10 minutes and the mixture was stirred at refluxing for 1 hour. The reaction mixture then was poured into 2% HCl (300 ml) and extracted with AcOEt (50 ml×3). The AcOEt layer was washed with H₂O, brine, and dried over Na₂SO₄. After the solvent was removed, the residue was purified by flash chromatography on silica gel eluted with Hexane/ AcOEt (2:1) to provide bianthraqunoyl 326 mg (81%).

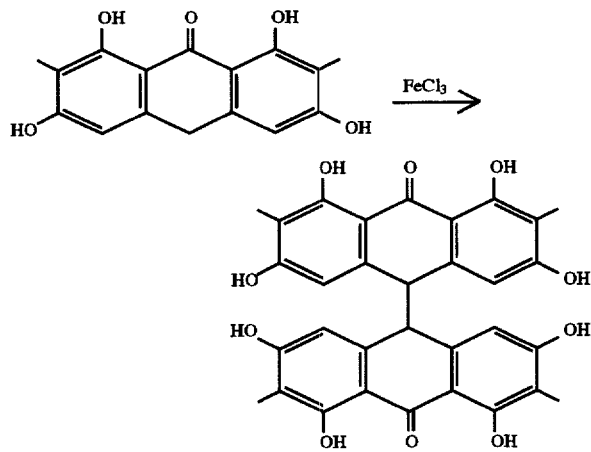

Analog D—Bisanthraquenone

To a solution of anthrone (40 mg, 0.14 mmol) in pyridine (1 ml), piperidine (90 mg), pyridine-N-oxide (100 mg) and FeSO₄ (5 mg) were added. The mixture was heated to 100° C. for 1 hour and poured into 100 ml of 3N HCl solution. The mixture was extracted with AcOEt (30 ml×3) and the AcOEt layer was washed with H₂O, and dried over Na₂SO₄. After solvent was removed under reduced pressure, the residue was purified by flash chromatography on silica gel eluted with Hexane/AcOEt (2:1), EtOAc, EtOAc/EtOH (7:1). The red fractions were combined to provide bisanthraquenone 25 mg (63%).

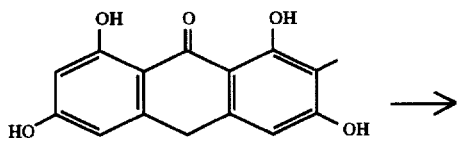

28

-continued

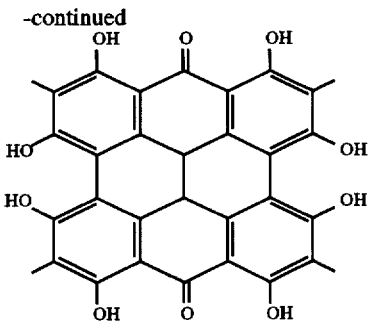

EXAMPLES 3–4

Synthesis of Precursors for Luciferin and Its Analogs

Precursor A—Benzothiazole

To a stirred solution of the methyl ester of 2-hydroxy-5-aminobenzoic acid was added ethylchlorooxalate (1.2 eq) in pyridine (1.3 eq) and in methylene chloride (1M) at 0° C. After stirring overnight, the solvent was removed and the residue was chromatographed using hexanes:ethyl acetate.

The diester amide (1 eq) was dissolved in acetic acid (1M). To this solution was added 1.2 eq of lead tetraacetate. A precipitate which developed was filtered, washed and taken on to the next step.

The iminoquinone (1 eq) was dissolved in pyridine (1M) and reacted with excess hydrogen sulfide at 0° C. After warming to RT overnight, the solution was heated to 50° C., cooled and concentrated in vacuo. The residue was purified by chromatography using ethyl acetate:methylene chloride to afford the benzothiazole in 45% yield over two steps. 2: NMR (CDCl₃): 1.17(t, J=7 Hz, 3H), 3.75(s, 3H), 4.25(q, J=7 Hz, 2H), 7.45(AB quartet, 2H).

Precursor B—benzothiazole hydroxy nitrile

To a solution of 1 equivalent of 2-chloro-6-alkoxybenzothiazole (C. G. Stuckwisch J. Am. Chem. Soc., 1949, 3417.) in DMSO (1M) was added 5 eq of sodium cyanide. The solution was heated to 80° C. for 8 h and then allowed to cool to RT overnight. After workup, the residue was purified by column chromatography using hexanes:ethyl acetate to form the cyano benzothiazole in 60% yield. The compound where R was methyl was identical to an authentic sample purchased from Aldrich Chemical Company.

The cyano benzothiazole (1 eq) was dissolved in methylene chloride (1M solution), cooled to 0° C. and treated with 1.5 eq of boron tribromide or excess boron trichloride gas. After allowing the solution to warm to RT overnight, the solvent was removed in vacuo and the residue was purified by chromatography using hexanes:ethyl acetate to produce benzothiazole hydroxy nitrile in 75% yield. The spectrum of this material was identical to material prepared by reaction with pyridinium hydrochloride (methyl ether case).

EXAMPLE 5

Synthesis of Luciferin and Its Analogs from Precursors

Precursors A and B synthesized above were each separately reacted with a substituted cysteine according to the method of White et al., *J. Am. Chem. Soc.*, 91,2178 (1969), incorporated herein by reference, to form luciferin or a luciferin analog.

EXAMPLES 6A–6D

Coupling of Activated Hypericin and Porphyrin Analogs with Luciferin Analogs to Form the Tethered Compounds 6A—From the anhydride of hypericin diacid To a 0.5M solution of hypericin anhydride (1.0 eq) in 1:1 methylene chloride/DMF at 0° C. is added a solution of the luciferin analog (1.1 eq). The solution is allowed to stir to RT over 5 hours. The solvents are removed in vacuo to afford the crude tethered molecule plus a small amount of luciferin analog. The crude product is partitioned between cold saturated sodium bicarbonate and ether. The aqueous layer is acidified with cold 1M HCl to afford the tethered molecule as an amorphous solid.

6B—From bis-bromomethyl hypericin

To a 1M solution of luciferin analog (1 eq) in 1:1 methylene chloride/DMF at 0° C. is added sodium hydride (1.0 eq). The suspension is stirred at 0° C. for 30 min and 1–2M solution of bis-bromomethyl hypericin (1 eq) in DMF is added at a rate of approximately 1 mmol/second. The reaction is allowed to warm to RT over 5 hours. The tethered molecule is isolated by concentrating the solution in vacuo followed by trituration with ether.

6C—From activated porphyrins

To a solution of 1 eq of protoporphyrin IX commercially available from Aldrech Chemical Company in 1:1 methylene chloride/DMF at RT is added dicyclohexylcarbodiimide (1 eq), followed by the luciferin analog (1 eq). The solution is stirred at RT for 8 hours. The solvents are removed in vacuo and the crude product is treated with cold saturated sodium bicarbonate and filtered to remove dicyclohexylurea. The aqueous layer is carefully acidified with cold 1M HCl. The tethered molecule separates as an amorphous solid.

6D—From pseudohypericin and "caged" luciferin

To a solution of luciferin (3 mg, 10.7 µmol) and HMM (2.2 mg, 21.8 µmol) in $CH_3CN$ (1 ml) at −15° C. was added benzyl chloroformate (3.8 mg, 22.3 µmol). The mixture was stirred at −15° C. for 15 min. and BtOH (1.5 mg, 11 µmol) was added. After 15 min., pseudohypericin (5 mg, 9.6 µmol) in DMF (0.4 ml) was added and the mixture was stirred at RT for 12 hr. The solvent was removed under reduced pressure at 23° C. and the dark residue was purified by chromatography on Sephadex LH-20 eluted with $CHCl_3$—MeOH—$H_2O$ (5:4:1) at 10° C. to provide the ester as a dark solid (3 mg).

EXAMPLE 7

Expression of Luciferase Under Control of EIAV Promoter

Luciferase was generated using a luciferase gene located in an expression plasmid constructed as explained below. The gene was under control of an EIAV long terminal repeat promoter. Plasmid DNA was introduced into equine cells in vitro and cell lysates were tested using functional assays of luciferase activity.

Materials and Methods

Figure 5:
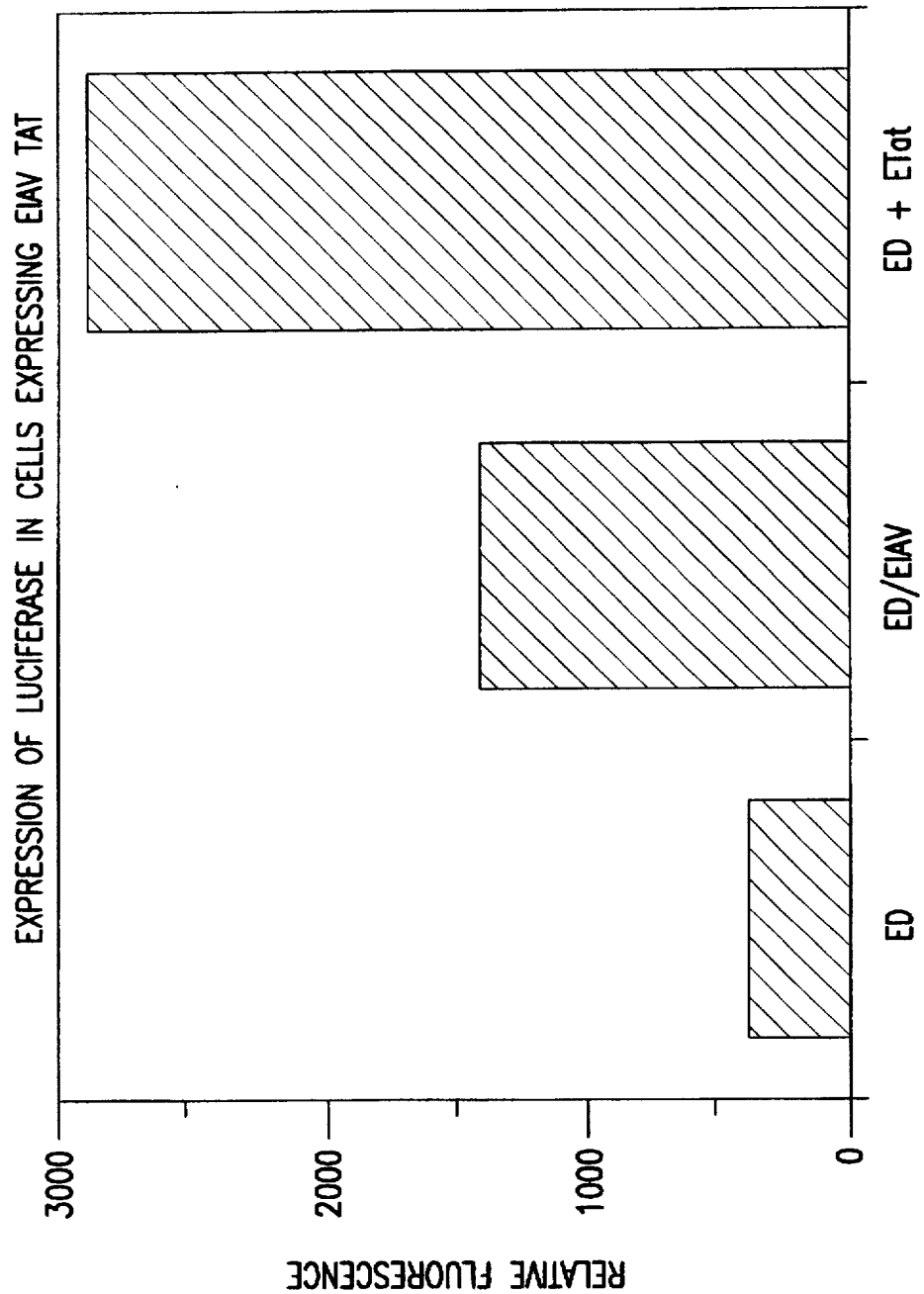
FIG. 5 shows the expression of luciferase in ED cells in the presence of EIAV or ETat.
Figure 6:
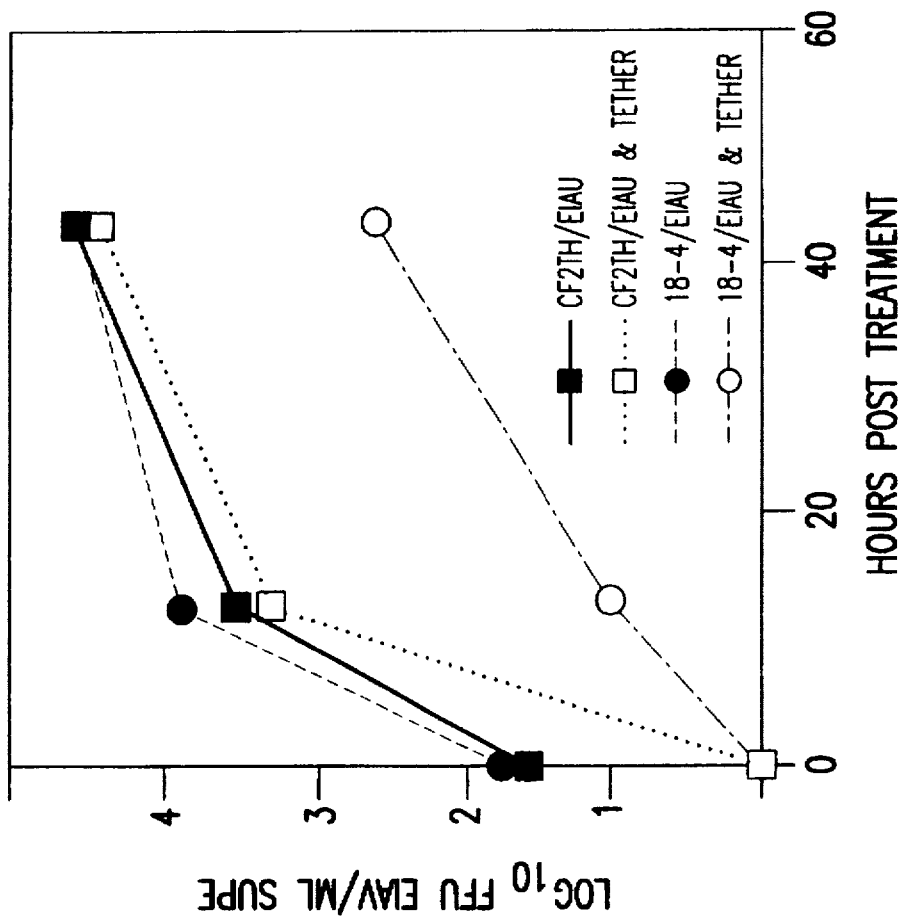
FIG. 6 shows 100–1000 fold reduction in virus production in infected cells treated with the expression plasmid of FIG. 3A and a tethered hypericin-luciferin compound according to the invention.

Plasmids. A complete proviral clone of the MA-1 isolate of EIAV in lambda EMBL4, designated EIAV 253, Carpenter et al., *J. Vir.* 65(3): 1605–1610 (1991), incorporated in its entirety herein by reference, obtained according to the methods disclosed in Carpenter et al. *J. Vir.*, 65(3): 1605–1610 (1991), was digested with EcoR1 and the proviral insert was ligated to EcoR1 restricted pUC19 using conventional cloning techniques. A plasmid containing the complete EIAV provirus, p26A, was identified by colony blot hybridization and restriction endonuclease digestion. p26A was digested with BstN1 and Nar 1 and the 322 base pair (bp) fragment containing the complete MA-1 long terminal repeat (LTR) and 4 bp of flanking sequences was separated by electrophoresis and isolated by electroelution. See Carpenter et al., *J Virol.,* 65(3): 1605–1610 (1991), FIG. 1, incorporated herein by reference, for the partial sequence of MA-1, which is also incorporated by reference. The LTR is located at positions 7909–8231. The ends were filled in with the Klenow fragment of *E. coli* DNA polymerase I, modified by the addition of HindIII linkers, ligated to HindIII restricted pUC19, and the fragment was transformed into *E. coli* JM109. Colonies containing the LTR insert were identified as before and individual plasmids were purified by replating. Plasmid DNA was isolated by ion exchange chromatography and the LTR fragment was excised by HindIII digestion and purified by electrophoresis and electroelution. The LTR fragment was ligated to HindIII restricted pGL-Basic (Promega Biotec, Madison, Wis.), transformed into JM109, and positive colonies identified by blot hybridization. Plasmid DNA was isolated from twelve of the hybridization positive colonies and the orientation of the LTR insert with respect to the luciferase gene was determined by restriction endonuclease digestion. Single clones containing the LTR insert in either the forward (pMA-1 LTR/LucF) or reverse (pMA-1LTR/LucR) orientation were selected for further analysis in functional assays of gene expression.

Additionally, a control plasmid having luciferase under control of the SV40 promoter, another plasmid encoding luciferase but no promoter, pGL2 Control and pGL2 Basic, were purchased from Promega Biotech (Madison, Wis.) for use in a luciferase assay. The plasmid, pRS Etat M, was provided by Dr. David Derse, National Cancer Institute, Frederick, Md. This plasmid expresses the EIAV transactivating protein, Tat, under the control of the Rous sarcoma virus promoter.

Transfection. Cells used for these studies included equine dermal (ED) cells (ATCC CCL57) and ED cells chronically infected with the MA-1 isolate of EIAV, Carpenter et al., *J. Virol.,* 65(3): 1605–1610 (1991) and Carpenter et al. *J. Virol.,* 63: 2492–2496 (1989), both of which are incorporated in their entirety by reference. For analysis of luciferase expression, cells were seeded in 60 mm tissue culture plates at $5\times10^5$ cells/plate and transfected the following day using Transfectase reagent (BRL). In most cases, cells were transfected with 10 μg of the luciferase expression plasmids (pMA-1 LTR/LucF, pMA-1 LTR/LucR, pGL2 control, or pGL2 basic) in the presence or absence of 100–300 ng pRS Etat-M. At 48 hr post-transfection, cells were lysed and assayed for luciferase expression using commercially available reagents (Promega). Comparable lysis buffers and assay reagents prepared in the laboratory were also tested.

Luciferase Assay. Assays for luciferase activity measure the production of light following the addition of the substrate, luciferin. Ten μl of cell lysate was mixed with 350 μl of reaction buffer containing 25 mM glycylglycine, pH 7.8, 5 mM ATP, 15 mM $MgSO_4$, pH 7.8, 4 mM EGTA, and 1 mM DTT. The samples were placed in an SLM 8000C spectrofluorometer, injected with 200 μl of 0.2 mM luciferin in 25 mM glycylglycine, 15 mM $MgSO_4$, 4 mM EGTA, 2 mM DTT, and light output was measured at 560 nm for 60 sec.

Results

Plasmids containing the MA-1 LTR upstream of the luciferase gene were obtained by standard cloning techniques as described above. Plasmids were functionally characterized in ED cells, in MA-1 infected ED cells, and in ED cells co-transfected with EIAV Tat (ETat). Only baseline levels of luciferase were expressed in ED cells in the absence of either virus infection or virus replication (FIG. 5). Expression of luciferase was detectable in both virus-infected cells, and in cells co-transfected with ETat. The values obtained from these experiments were extrapolated to a standard curve derived using known molar concentrations of commercially available luciferase (Sigma, St. Louis, Mo.). The molar concentrations of luciferase in the cell lysates ranged between $1.8 \times 10^{-13}$ to greater than $3 \times 10^{-12}$M. The relatively low levels of luciferase were likely due to the low transfection efficiency of ED cells (Carpenter, unpublished observations).

EXAMPLE 8

Sythesis of Dioxetane and Formation of Dioxetane Tethered Compound

Aldehyde phencol C was silylated using tert-butyldimethylchloro silane (TBSCl) and imidazole at room temperature in dimethylformamide (DMF) as solent. The resulting silylated aldehyde was then treated with triethyl phosphite and trimethylchlorosilane (TMSCl) to provide a phosphonate which will then react with adamantanone to furnish ketone D. The base used in this process can be potassium tertbutoxide or preferably, n-butyl lithium. This reaction must be conducted in an aprotic solvent such as tetrahydrofuran (THF) or diethyl ether at subambient temperatures.

Reduction of ketone D using samarium iodide in THF-methanol (MeOH) at −78° C. provided ketone E in an excellent yield. Formation of the enol ether F was readily accomplished by treatment of ketone E with a strong base (potassium tert-butoxide or sodium hydride) in an aprotic solvent (THF) followed by an alkylating agent such as methyl iodide, dimethyl sulfate, dibromoethane or chloromethyl 2-bromoethyl ether. This reaction proceeded best at subambient temperatures. Formation of dioxetane H was achieved by reacting the enol ether with excess oxygen and a sensitizer such as methylene blue. Alternatively, the enol ether was reacted with the complex formed from ozone and triphenyl phosphite from −40° C. to room temperature. The complex formed from ozone and triphenyl phosphite has been shown to generate singlet oxygen at temperatures above −40° C.

In the case of compound B wherein R is CH$_2$Br, the substitution of the bromide by a photoactive (light-accepting) molecule (e.g. protoporphyrin or hypericin) will generate the dioxetane I. In this specific case, the "trigger" is the TBS group which will be activated by fluoride ion.

EXAMPLE 9

Assessment of Antiviral Activity in Cells

As a model system for development of inducible chemiluminescence, we constructed a further plasmid containing the promoter region of EIAV inserted upstream of the gene for luciferase (pMA-1LTRLuc). Calcium phosphate co-precipitation was used to co-transfect Cf2th cells with pMA-1LTRLuc and pSVNeo5, and cells were selected for neomycin resistance using G418. Resistant cells were expanded, analyzed for the presence of pMA-1LTRLuc using the polymerase chain reacation (PCR). Cells containing the luciferase gene were transfected with an EIAV Tat expression plasmid and tested for expression of luciferase activity in transient expression assays. Twelve of 24 cell lines derived from single-cell clones were positive by both assays. These cells were subcultured, and parallel cultures were infected with the MA-1 isolate of EIAV. Initial assays were done to determine if incresed levels of luciferase expression occurred in virus-infected cells. Results (Table 1) indicated that luciferase expression increased 10–1000 fold in virus-infected cells, as compared to non-infected cells, thus demonstrating the targeting of hypericin activation to infected cells. The matched cell lines 18-4 and 18-4/MA-1 provided a useful model to assess the chemiluminescent activation of hypericin in reducing production of a lentivirus in cells expressing luciferase.

TABLE 1

Fold-transactivation of luciferase expression by EIAV in stable cell lines transfected with pMA-1LTRLuc

| CELL CLONE | nM LUCIFERASE | | FOLD-INCREASE |
|---|---|---|---|
| | Uninfected | MA-1 Infected | |
| 13-2 | 0.13 | 1.9 | 15 |
| 13-4 | 0.008 | 0.95 | 118 |
| 14-1 | 0.14 | 1.0 | 7 |
| 14-2 | 0.19 | 1.5 | 7 |
| 14-3 | 0.02 | 1.1 | 55 |
| 17-1 | 0.007 | 0.65 | 9 |
| 17-4 | 0.017 | 1.7 | 100 |
| 18-1 | 0.015 | 0.66 | 44 |
| 18-2 | 0.023 | 2.1 | 91 |
| 18-3 | 0.006 | 0.74 | 123 |
| 18-4 | 0.002 | 2.0 | 1,000 |
| 19-1 | 0.016 | 1.5 | 94 |

CF2th cells infected with EIAV (Cf2th/EIAV) and EIAV-infected Cf2th cells expressing the luciferase gene (18-4/EIAV) were seeded in duplicate in a six-well tissue culture plate. At two days, culture supernatant was removed and the cells were washed 3× with cell culture media. The remainder of the experimental protocols were completed in very subdued light. One well each of Cf2th/EIAV and 18-4/EIAV were treated with the tether molecule of Example 6D, 60 μg in 3 ml media. The other wells served as non-treated controls. Cells were incubated at 37° C. for one hour, media was aspirated, and cells were washed 3× and fresh media was added. At 0, 13, and 44 hours, culture supernatant was sampled from each well and virus production was quantitated using a focal immunoassay. Briefly, equine dermal cells were inoculated with serial ten-fold dilutions of supernatant samples, and after five days foci of infectious virus was detected by immunocytochemistry.

Results indicated that production of infectious virus was reduced 100–1000 fold in 18-4/EIAV cells treated with the tether; no reduction in infectious virus was observed in Cf2th/EIAV (FIG. 6). These results demonstrate that treatment of lentivirus-infected cells expressing the luciferase gene with a hypericin-luciferin tether generates sufficient chemiluminescence to activate the antiviral activity of hypericin. Subsequent experiments have repeatedly shown that production of infectious virus is reduced approximately 90% in 18-4/MA-1 cells as compared to Cf2th/MA-1 cells.

EXAMPLE 10

Preparation of Retroviral Vectors and Destruction of Neoplastic Cells

Construction of Retroviral Vectors for Gene Therapy:

The retroviral plasmid vector pLXSN is used for construction of a viral vector for in vitro and in vivo delivery of the luciferase gene. Cell-specific regulation of luciferase expression can be achieved using specific promoters to regulate luciferase transcription. For treatment of HIV infections, a suitable promoter contains the HIV TAR and upstream Sp-1 and NF-kB sites, as shown in FIG. 3B. An example, as shown in FIG. 3C, of tumor-specific expression includes the use of the tissue-specific tyrosinase promoter for treatment of primary and metastatic melanoma. See, e.g., Vile et al., *Cancer Res.*, 54, pp. 6228–6234 (1994), Vile and Hart, *Cancer Res.*, 53, pp. 3860–3864 (1993), each of which is incorporated herein in its entirety by reference. In all cases, construction of retroviral vectors follows general procedures, as follows. pLXSN contains NEOr for selection of producer clones and target cells. NEOr is driven from the SV40 early promoter, and an upstream multiple cloning site is available for insertion of a luciferase/promoter cassette. In general, pLXSN is linearized and ligated to gene cassettes using BamH1. Following transformation, colonies are screened by hybridization using insert-specific probes radiolabelled with $^{32}P$, and positive colonies are characterized by restriction enzyme digestion and nucleotide sequence analysis.

For production of virus, plasmids are introduced into the packaging cell line PA317 (ATCC CRL 9078) using the calcium phosphate method of transfection. Two days following infection, cells are subcultured in the presence of 2 mg/ml G-418, and producer cell clones are isolated using cloning rings. Each clone is initially tested for production of vector virus using a reverse transcriptase assay (Carpenter and Kraus, 1991). Clones shown to produce packaged vector virus are further analyzed for their ability to transfer neomycin resistance to NIH/3T3 cells. Supernatant is serially diluted and inoculated in duplicate onto NIH/3T3 cells in polybrene (8 μg/ml). Cells are cultured in the presence of G-418 for 7–10 days, at which time the cells are stained with methylene blue and the number of neomycin resistant clones is quantitated. Clones with a titer greater than $10^5$ are expanded, and DNA is isolated for Southern analysis of the vector sequences. For production of supernatant, producer cells are seeded in 75 $cm^2$ flasks and grown until 80–90% confluent at which time media is aspirated and replaced with 20 ml fresh media. Supernatant is collected at 24 hours intervals for three days, clarified by centrifugation, aliquotted, and stored at −70° C.

Assays for Antiviral Activity:

Supernatants from high producer packaging cell clones are inoculated onto target cells in 8 μg/ml polybrene. Following transduction, cells are cultured in the presence of G-418 (Sigma Chemical Co.) in order to select for clonal populations of transduced cells. Expanded clones are assayed for luciferase expression as described above. Cell clones found to express high levels of luciferase are infected with virus as before and incubated with 30 μg/ml tethered molecule for 30 min in the dark. Following treatment, culture supernatant is sampled daily and assayed for quantity of infectious virus.

Assays for Tumor Cell Cytotoxicity:

Tumor cell cytotoxicity is tested using B16-F1 murine melanoma cells (ATCC CRL 6323) and NIH3T3 (ATCC CRL 1658) fibroblasts as positive and negative controls, respectively. Supernatants from high producer packaging cell clones are inoculated onto target cells in 8 μg/ml polybrene. Following transduction, cells are cultured in the presence of G-418 in order to select for clonal populations of transduced cells. Expanded clones are assayed for luciferase expression as described above. Cell clones found to express high levels of luciferase are incubated with 30 μg/ml tethered molecule for 30 min in the dark, and 10-fold serial dilutions are plated in medium containing G-418.

After 10 days, tumor cell cytotoxicity is evaluated by counting the number of surviving cell clones in tether-treated cultures versus non-treated cultures (Vile and Hart, 1993).

While the invention has been described with reference to specific embodiments, it will be apparent to those skilled in the art that many alternatives, modifications, and variations may be made. Accordingly, it is intended to embrace all such alternatives, modifications, and variations that may fall within the spirit and scope of the appended claims.

We claim:

1. An antiviral composition comprising:
   a. a photosensitizing chemical means for inactivating a virus, wherein said photosensitizing means is activated by absorbing light or energy within a specific wavelength range; and
   b. an energy donating chemical means for activating the virucidal activity of said photosensitizing means, wherein said energy donating means, when activated, tranfers energy or emits light within the range of that absorbed by said photosensitizing means.

2. The composition of claim 1 further comprising activating means for activating the transfer of energy or the emission of light from said energy donating means.

3. The composition of claim 2 wherein said means for activating said transfer or emission comprises an expression plasmid containing a gene encoding luciferase or another activating chemical means.

4. The composition of claim 3 wherein said gene is under the control of a promoter that is transactivated by replication of said virus.

5. The composition of claim 4 wherein said virus is a lentivirus and wherein said promoter is a lentivirus long terminal repeat or a portion thereof.

6. The composition of claim 1 wherein said photosensitizing means and said energy donating means are connected to each other by a chemical tether.

7. The composition of claim 6 wherein said photosensitizing means and said energy donating means comprise a tethered compound having the following formula:

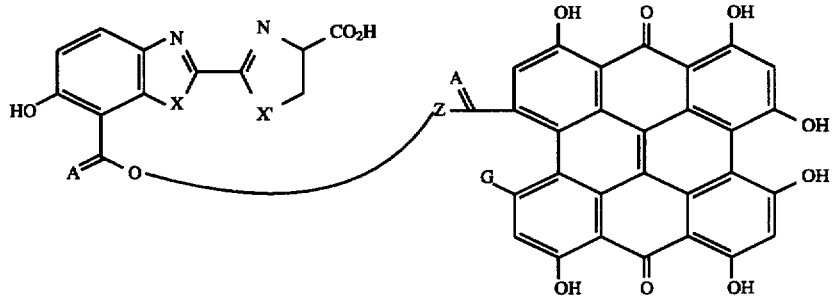

wherein $R_1$ is said tether and X and X' are defined as in claim 8; and wherein $R_1$ is —$CO_2(CH_2)_nZ$, wherein n is 2 to 15; $R_2$–$R_4$ are H; Z is O, NH or S; A is O or H,H; and G is $CH_3$, $CO_2H$, $CO_2Me$ or $CH_2Br$.

8. The composition of claim 6 wherein said photosensitizing means and said energy donating means comprise a tethered compound having the following formula:

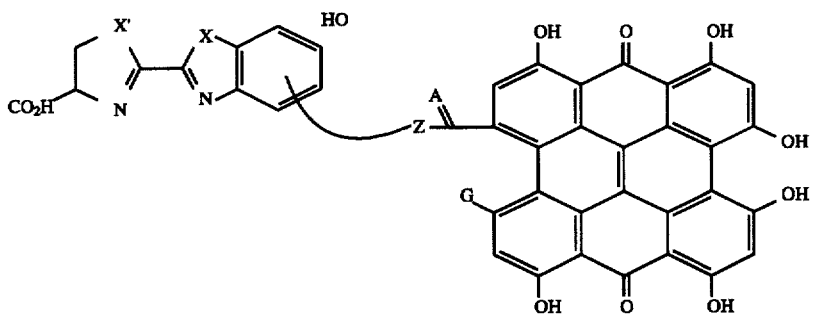

wherein $R_2$ is said tether, and X and X' are defined as in claim 8; and wherein $R_2$ is selected from the group consisting of —$(CH_2)_nCOZ$ and —$S(CH_2)_nZ$, wherein n is 1 to 15; $R_1$, $R_3$ and $R_4$ are H; Z is O, NH or S; A is O or H,H; and G is $CH_3$, $CO_2H$, $CO_2Me$ or $CH_2Br$.

9. The composition of claim 6 wherein said photosensitizing means and said energy donating means comprise a tethered compound having the following formula:

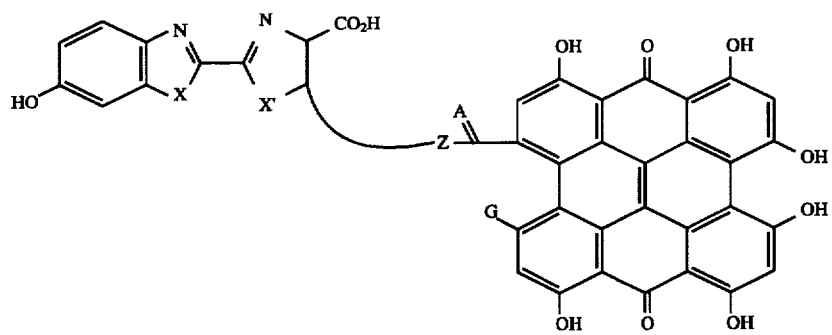

wherein $R_3$ is said tether and X and X' are defined as in claim 8; and $R_3$ is selected from the group consisting of —COZ and —$(CH_2)_nZ$, wherein n is 1 to 15; $R_1$–$R_2$ and $R_4$ are H; Z is O, NH, or S; A is O or H,H; and G is $CH_3$, $CO_2H$, $CO_2Me$ or $CH_2Br$.

10. The composition of claim 6 wherein said photosensitizing means and said energy donating means comprise a tethered compound having the following formula:

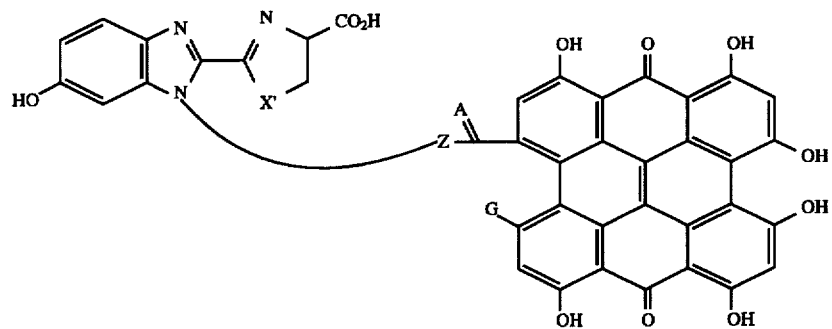

wherein $R_4$ is said tether and X is defined as in claim 8; and $R_4$ is —$(CH_2)_nZ$, wherein n is 2 to 15; $R_1$–$R_2$ and $R_4$ are H; Z is O NH, or S; A is O or H,H, and G is $CH_3$, $CO_2H$, $CO_2Me$ or $CH_2Br$.

11. The composition of claim 6 wherein said tethered compound has the following formula:

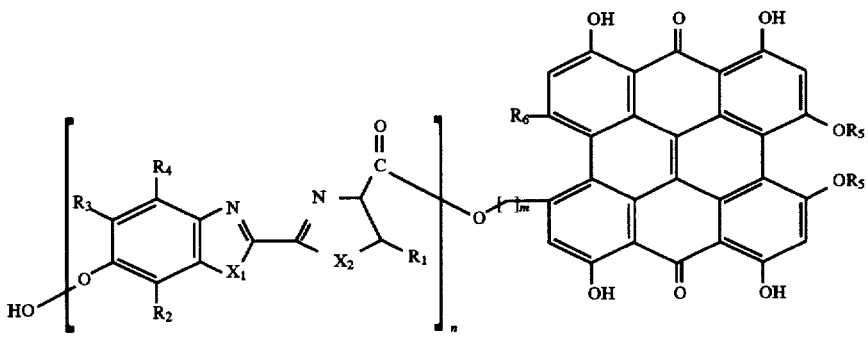

wherein R is H, an alkyl or aryl; $R_2$ and $R_3$ are H, OH, Cl, CN or an alkyl; $R_4$ is H, OH, an alkyl or aryl; $R_5$ is H or $CH_3$;

$R_6$ is H, OH, Cl or an alkyl; $X_1$ is O, N-alkyl, N-aryl or S; $X_2$ is O, N-alkyl or S; n is 1 to 10; and m is 1 to 4.

12. The composition of claim 1 wherein said photosensitizing means is selected from the group consisting of hematoporphyrin analogs, polycyclic quinones, phthalocyanines and porphyrins.

13. The composition of claim 12 wherein said photosensitizing means is hypericin or an analog thereof.

14. The composition of claim 13 wherein said hypericin analog has the following formula:

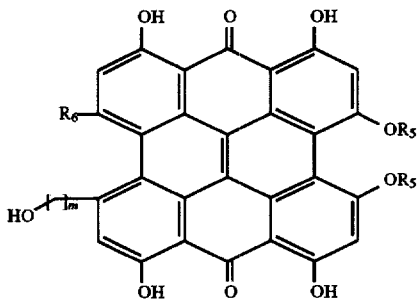

wherein $R_5$ is H or $CH_3$; $R_6$ is H, OH, Cl or an alkyl; and wherein m is 1–4.

15. The composition of claim 1 wherein said energy donating means is luciferin, an analog thereof or a dioxetane.

16. The composition of claim 15 wherein said luciferin analog has the following formula:

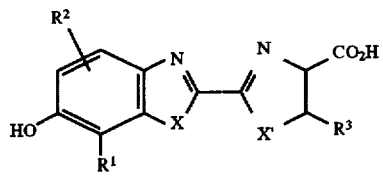

wherein $R_1$, $R_2$, $R_3$ or $R_4$ is said tether, wherein X and X' are selected from the group consisting of S, O, H,H, CH=CH or $NR_4$;

if $R_1$ is said tether, $R_1$ is —$CO_2(CH_2)_nY$, wherein n is 2 to 15; $R_2$–$R_4$ are H; and Y is OH, SH, $NH_2$;

if $R_2$ is said tether, $R_2$ is —$(CH_2)_nCO_2H$ and —$S(CH_2)_{n+1}Y$, wherein n is 1–15; $R_1$ and $R_3$–$R_4$ are H; and Y is OH, $NH_2$ or SH;

if $R_3$ is said tether, $R_3$ is selected from the group consisting of —$CO_2H$ and —$(CH_2)_nY$, wherein n is 1–15; $R_1$, $R_2$ and $R_4$ are H; and Y is OH, $NH_2$ or SH; and if $R_4$ is said tether, $R_4$ is —$(CH_2)_nY$, wherein n is 2–15; $R_1$–$R_3$ are H; and Y is OH, $NH_2$ or SH.

17. The composition of claim 15 wherein said dioxetane has the following formula

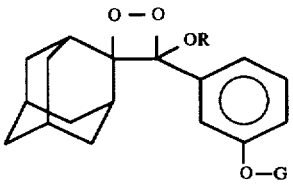

wherein R is said photosensitizing means and G is a trigger means for reacting with a compound produced by said virus, wherein said reaction activates said dioxetane.

18. The composition of claim 15 wherein said dioxetane has the following formula

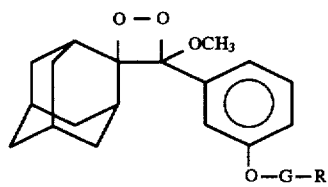

wherein R is said photosensitizing means and G is a trigger means for reacting with a compound produced by said virus, wherein said reaction activates said dioxetane.

* * * * *